United States Patent [19]

Emoto et al.

[11] Patent Number: 5,114,614

[45] Date of Patent: May 19, 1992

[54] LIQUID CRYSTAL COMPOSITION

[75] Inventors: Naoyoshi Emoto; Hideo Saito, both of Yokohamashi; Kenji Furukawa, Yokosukashi, all of Japan

[73] Assignee: Chisso Corporation, Osaka, Japan

[21] Appl. No.: 231,527

[22] Filed: Aug. 12, 1988

Related U.S. Application Data

[62] Division of Ser. No. 890,653, Jul. 30, 1986, Pat. No. 4,780,240.

[30] Foreign Application Priority Data

| Aug. 2, 1985 | [JP] | Japan | 60-170951 |
| Aug. 5, 1985 | [JP] | Japan | 60-172090 |
| Oct. 17, 1985 | [JP] | Japan | 60-232219 |
| Nov. 15, 1985 | [JP] | Japan | 60-255866 |
| Mar. 19, 1986 | [JP] | Japan | 61-61691 |
| Mar. 19, 1986 | [JP] | Japan | 61-61692 |

[51] Int. Cl.$^5$ .............. C09K 19/12; C09K 19/20; C09K 19/34; C09K 19/30

[52] U.S. Cl. .............. 252/299.65; 252/299.01; 252/299.6; 252/299.61; 252/299.63; 252/299.64; 252/299.66; 252/299.67; 252/299.68

[58] Field of Search .......... 252/299.01, 299.6, 299.61, 252/299.63, 299.64, 299.65, 299.66, 299.67, 299.68

[56] References Cited

U.S. PATENT DOCUMENTS 3,792,915  2/1974  Soo Oh et al. ................. 252/299.01

(List continued on next page.)

OTHER PUBLICATIONS

Flussige Kristalle in Tabellen, Demus, D. Ed., VEB Deutscher Verlag für Grundstoffindustrie, Leipzig, pp. 65-68, 1974.

Gray, G. W. et al., Mol. Cryst. Liq. Cryst., 48(1-2), 37, 1978.

(List continued on next page.)

Primary Examiner—John S. Maples
Assistant Examiner—Philip Tucker
Attorney, Agent, or Firm—Wenderoth, Lind & Ponack

[57] ABSTRACT

A nematic liquid crystal composition having a notable increase of the twistability (i.e. the reciprocal of the intrinsic helical pitch) with temperature rise is provided, which composition comprises (i) optically active substance(s) which are the same in the helical twist sense to one another and make positive the temperature dependency of the twistability of the cholesteric phase induced when singly added to nematic compound(s), and (ii) nematic liquid crystal(s), which optically active substance(s) are a specificed compound (I) containing a plurality of benzene, cyclohexane, dioxane, pyrimidine or/and pyridine ring and also having an optically active terminal group

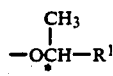

($R^1$: alkyl); and further a nematic composition having a nearly constant twistability with temperature rise is provided, which composition comprises the above compound (I), optically active substance(s) which have the same helical twist sense as that of (I) and make negative the temperature dependency of the twistability of the induced cholesteric phase when singly added to nematic compound(s) and nematic liquid crystal(s), which latter optically active substance(s) are a specified compound (II) containing a plurality of benzene, cyclohexane dioxane, pyrimidine or/and pyridine group and having an optically active terminal group

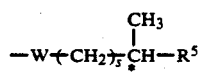

(W: a specified group, S: 0-4, and $R^5$: alkyl).

8 Claims, 15 Drawing Sheets

U.S. PATENT DOCUMENTS

| | | | |
|---|---|---|---|
| 3,923,685 | 12/1975 | Soo Oh et al. | 252/299.01 |
| 4,143,947 | 3/1979 | Aftergut et al. | 350/334 |
| 4,264,148 | 4/1981 | Göbl-Wunsch et al. | 350/346 |
| 4,668,427 | 5/1987 | Saito et al. | 252/299.66 |
| 4,689,176 | 8/1987 | Inoue et al. | 252/299.65 |
| 4,761,246 | 8/1988 | Inukai et al. | 252/299.68 |
| 4,765,924 | 8/1988 | Inoue et al. | 252/299.61 |
| 4,801,756 | 1/1989 | Kano et al. | 252/299.01 X |
| 4,818,430 | 4/1989 | Saito et al. | 252/299.61 |
| 4,824,597 | 4/1989 | Kano et al. | 252/299.61 |
| 4,826,621 | 5/1989 | Terashima et al. | 252/299.61 |
| 4,834,907 | 5/1989 | Inoue et al. | 252/299.65 |
| 4,835,274 | 5/1989 | Kano et al. | 252/299.01 X |
| 4,865,763 | 9/1989 | Inoue et al. | 252/299.61 |
| 4,866,199 | 9/1989 | Shibata et al. | 252/299.01 X |
| 4,880,936 | 11/1989 | Sasaki et al. | 546/339 |
| 4,886,622 | 12/1989 | Miyazawa et al. | 252/299.61 |
| 4,911,861 | 3/1990 | Higuchi et al. | 252/299.65 |
| 4,925,592 | 5/1990 | Kano et al. | 252/299.67 |
| 4,946,989 | 8/1990 | Kawamura et al. | 252/299.67 X |
| 4,959,173 | 9/1990 | Shibata et al. | 252/299.65 |
| 4,961,874 | 10/1990 | Takeuchi et al. | 252/299.6 |
| 4,980,082 | 12/1990 | Ohba et al. | 252/299.61 |
| 4,980,083 | 12/1990 | Shibata et al. | 252/299.61 |
| 4,988,458 | 1/1991 | Heppke et al. | 252/299.63 |
| 4,997,942 | 3/1991 | Osawa et al. | 252/299.01 X |

FOREIGN PATENT DOCUMENTS 284093  9/1988  European Pat. Off. ........ 252/299.61

OTHER PUBLICATIONS

Schaeffer et al., 1985 SID International Symposium Digest of Technical Papers, pp. 120–123.

Nakagawa et al., SID International Symposium Digest of Technical Papers, pp. 78–80.

Baur et al., 15 Freiburger Arbeitstagung Flüssigkristalle (Mar. 1985).

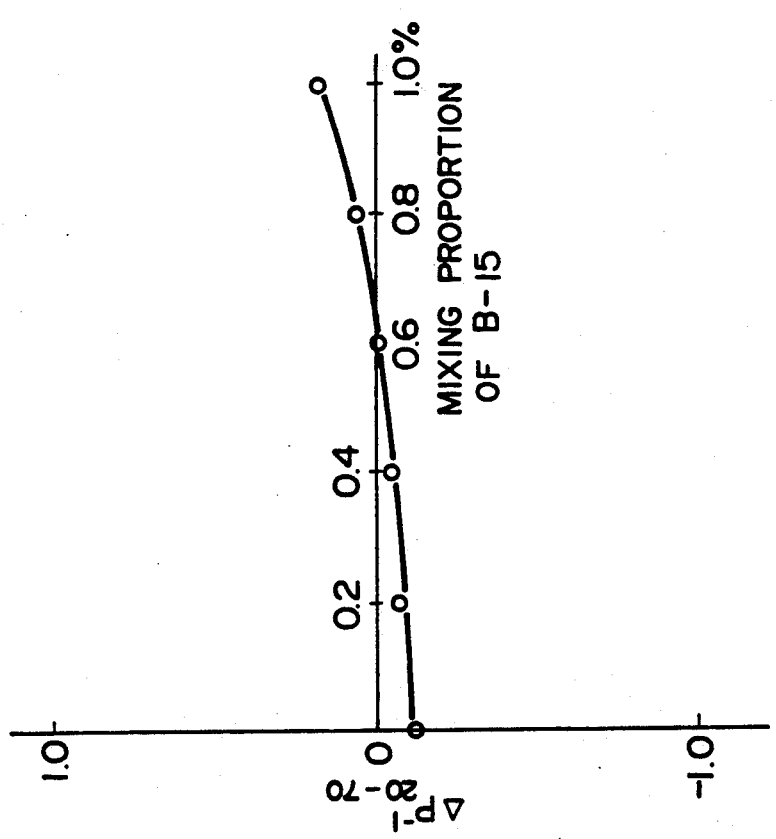
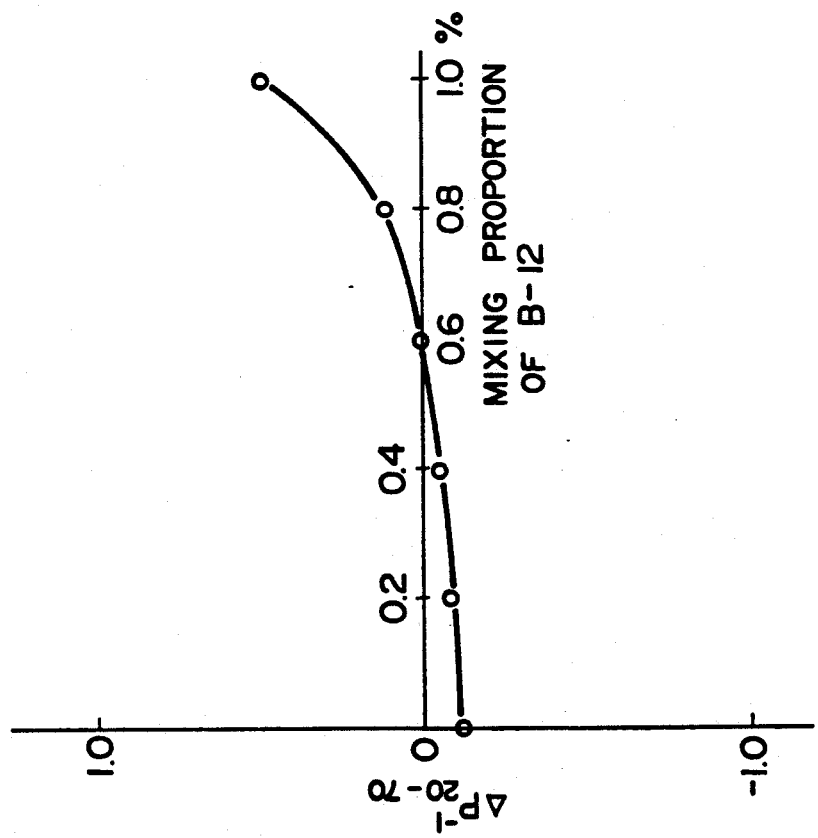

LIQUID CRYSTAL COMPOSITION

This is a division of application Ser. No. 06/890,653, filed Jul. 30, 1986, now U.S. Pat. No. 4,780,240.

BACKGROUND OF THE INVENTION

1. Field of the Invention

This invention relates to a nematic liquid crystal composition. More particularly, it relates to a nematic liquid crystal composition which, when used for liquid crystal display elements, improves the temperature dependency of the threshold voltage thereof and also improves the temperature dependency of the intrinsic helical pitch (hereinafter referred to as "P").

2. Description of the Prior Art

As to TN type liquid crystal display elements, their use applications have been rapidly enlarged due to improvements in circuit, driving mode and cell preparation technique and particularly improvement in the characteristics of liquid crystal compositions sealed in the elements, although their use applications has been directed only to watches, electric calculators, etc. in theirs initial use.

Such a rapid enlargement of the use applications due to improvements in liquid crystal compositions and others owes a great deal to ① increase in the display capacity and ② broadening of the temperature range of the nematic liquid crystal phase.

With respect to the increase in the display capacity, displays of hand-held computors and liquid crystal television are illustrated as use applications. With respect to the broadening of the temperature range of nematic liquid crystal phase, displays for instruments used on cars and instruments for outdoor use are illustrated. However, there are a large number of matters to be improved for liquid crystal display elements. Examples of such matters are narrow angle of view, inferior contrast, low response speed, still yet small display capacity, reduction in the display quality due to ambient temperature change, etc. Among these, the reduction in the display quality due to ambient temperature change is attributed to the change in the threshold voltage $V_{th}$ depending on temperature.

In order to suppress the occurrence of the reverse twist of liquid crystal molecules to thereby retain the display quality of liquid crystal display elements, it has been very usually carried out to add a slight quantity of an optically active substance having a clockwise or counterclockwise helical twist sense. However, there is a problem that since the threshold voltage of liquid crystal compositions still yet has a considerable temperature dependency, reduction in the display quality due to ambient temperature change is unavoidable.

With respect to improvements in the angle of view and contrast, considerable improvements have been made by employing supertwisted birefringence effect mode (abbreviated to SBE). SBE mode is different in certain points from TN mode. Firstly, according to TN mode, addition of a slight quantity of an optically active substance helps the glass substrates subjected to aligning treatment to twist liquid crystal molecules by 90° between substrate due to their anchoring action. Here, the ratio (P/d) of the intrinsic helical pitch (P) of liquid crystal composition to the cell thickness (d) of display element is usually about 10~20. According to SBE mode, however, by increasing the quantity of an optically active substance added to a large extent to thereby make the value of P/d 2 or less, the liquid crystal molecule is twisted by 270°. Further, according to TN mode, liquid crystal molecules are aligned in a state where no voltage is impressed, inside the display element, so as to give an angle of liquid crystal molecule made against glass substrates (pre-tilt angle) within several degrees, whereas according to SBE mode, alignment is made so as to give a pre-tilt angle of about 20°. An example of having improved the angle of view and contrast according to such SBE mode has been reported (T.J. Scheffer, J. Nerhring, M. Kaufmann, H. Amstutz, D. Heimgartner and P. Eglin, Society for Information Display, 1985, International Symposium).

However, this SBE mode, too, raises a problem. Namely, since the intrinsic helical pitch P varies depending on the temperature change, it occurs that when the value of P/d exceeds 2, 270° twist is changed to 90° twist; hence it is necessary to keep the intrinsic helical pitch P at a constant value irrespective of temperature.

Further, with respect to improvement in the display capacity, it is necessary to improve the steepness of change in the transmittance in the case where a voltage is impressed to the display element. G. Bauer and W. Fehrenbach reported a calculation result that the steepness is improved to a large extent at 270° twist (15. Freiburger Arbeitstagung Flüssigkristalle (1985)). In this case, too, it is necessary to be free from change in the intrinsic helical pitch depending on the temperature change.

With respect to the improvement in the response speed, Nakagawa and Masuda reported that response speed has been improved by employing a double-layered guest-host mode (abbreviated to DGH mode) wherein two pieces of a liquid crystal display element of guest-host type are placed on one another and liquid crystal compositions having P/d=1.0 (i.e. 360° twist) are employed. (Nakagawa and Masuda, Society for Information Display, 1985 International Symposium). In this case, too, it is important to be free from change in the intrinsic helical pitch depending on the temperature change.

Further, in the display elements of the phase transition mode (PC mode), too, it is better to be free from change in the intrinsic helical pitch depending on the temperature change. Further, with respect to overcoming reduction in the display quality depending on ambient temperature change, this may be effected by reducing the temperature dependency of the threshold voltage $V_{th}$.

As to the cause of change in the threshold voltage $V_{th}$ depending on the temperature range, changes in the elastic constant of nematic liquid crystals, the dielectric anisotropy, etc. depending on the temperature change, change in the intrinsic helical pitch depending on the temperature change, etc. are enumerated. In order to improve the temperature dependency of the threshold voltage, certain attempts have been made, and among these, a process of improving the temperature dependency of the threshold voltage by controlling change in the intrinsic helical pitch depending on the temperature change has often been carried out.

When an optically active substance is added to a nematic liquid crystal, there is the following equation (1) between the concentration C of the optically active substance and the intrinsic helical pitch P of the resulting liquid crystal composition, and in addition, the reciprocal of the intrinsic helical pitch $P^{-1}$ is also referred to as "twistability" and exhibits the strength of twist:

$$P^{-1} = h \cdot C \quad (1)$$

wherein h is referred to as helical twisting power and a constant intrinsic of the optically active substance and varies depending on temperature. The change of h depending on the temperature change is expressed by the following equation (2):

$$h = \alpha + \beta T + \gamma T^2 + \cdots \quad (2)$$

wherein $\alpha, \beta, \gamma, \cdots$ each represent a proportionality factor.

An example of the twistability ($P^{-1}$) dependency of the threshold voltage $V_{th}$ in the case where the temperature is constant and also the cell thickness of the TN type liquid crystal element is constant, is shown in FIG. 1. FIG. 1 shows the relationship between the twistability ($P^{-1}$) and the threshold voltage $V_{th}$ in the case where an optically active substance C-1 expressed by

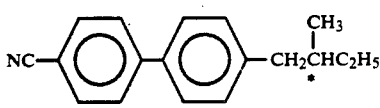

is added to a nematic liquid composition A shown below:

n-C$_3$H$_7$—⟨⟩—⟨⟩—CN  24 wt. % n-C$_5$H$_{11}$—⟨⟩—⟨⟩—CN  36 wt. % n-C$_7$H$_{15}$—⟨⟩—⟨⟩—CN  25 wt. % n-C$_5$H$_{11}$—⟨⟩—⟨⟩—⟨⟩—CN  15 wt. %

As seen from FIG. 1, the threshold voltage $V_{th}$ rises with an increase of the twistability ($P^{-1}$). Namely, the longer the intrinsic helical pitch P of the liquid crystal composition becomes, the more the threshold voltage $V_{th}$ is reduced.

Further, the temperature dependency of the twistability ($P^{-1}$) in the case where the optically active substance C-1 is added in 0.4% by weight to the above nematic liquid crystal composition A is shown in FIG. 2. As seen from FIG. 2, the twistability ($P^{-1}$) decrease with temperature rise, and the intrinsic helical pitch P of the liquid crystal composition increase with temperature rise.

On the other hand, the temperature dependency of the threshold voltage $V_{th}$ is shown in FIG. 3. The threshold voltage $V_{th}$ lowers with temperature rise. This indicates that as seen from FIG. 1 and FIG. 2, the intrinsic helical pitch P of the liquid crystal composition increases with temperature increase to thereby lower the threshold voltage $V_{th}$. Further, it has been known that the threshold voltage $V_{th}$ lowers depending on decrease in the elastic constant of the composition due to the temperature rise.

Thus, in order to reduce the temperature dependency of the threshold voltage $V_{th}$, the intrinsic helical pitch P of the liquid crystal composition is preferred to be shorter with the temperature rise.

As apparent from the foregoing, control of the temperature dependency of the intrinsic helical pitch is very important for overcoming various problems raised on the liquid crystal display elements of various display modes. Namely, as to SBE mode, DGH mode and PC mode, the intrinsic helical pitch has been required to be constant irrespective of temperature. Further, in order to improve the temperature dependency of the threshold voltage in the case of TN mode, the intrinsic helical pitch has been required to be shorter with the temperature rise. However, too steep reduction in the cholesteric pitch with temperature rise is not always satisfactory; thus it is also necessary to adjust the extent of the change of the intrinsic helical pitch depending on the temperature change. However, if a generally known optically active substance is added, the intrinsic helical pitch of the resulting nematic liquid crystal composition increases with the temperature rise. In short, the twistability ($P^{-1}$) decreases with temperature rise; hence, even if the substance alone is added, it is impossible to control the temperature dependency of the intrinsic helical pitch. That is, it is impossible to be free from the temperature dependency of the intrinsic helical pitch or to obtain a temperature dependency which is contrary to the conventional one.

When a plurality of optically active substances are added to nematic liquid crystals, the intrinsic helical pitch $P_{Mix}$ of the resulting liquid crystal composition is expressed by the following equation (3):

$$P_{Mix}^{-1} = \sum_{i=1}^{n} hi \cdot Ci = \sum_{i=1}^{n} P_i^{-1} \quad (3)$$

This equation (3) indicates that the $P_{Mix}^{-1}$ of the final liquid crystal composition is the sum of the respective $P_i^{-1}$s obtained when the respective optically active substances are singly added to the original nematic liquid crystals in a concentration of $C_i$.

In addition, when the symbol h of helical twisting power is made positive relative to right-twisted optically active substance and made negative relative to left-twisted optically active substance, the intrinsic helical pitch $P_{Mix}$ of the liquid crystal composition obtained by adding the mixture of right-twisted and left-twisted optically active substances to nematic liquid crystals is also expressed by the equation (3).

In the case of conventional optically active substances, even if two optically active substances each having a twist in the same sense are mixed and the mixture is added to nematic liquid crystals, the resulting temperature dependency of the intrinsic helical pitch is nothing but an intermediate one between the two dependencies derived from the respective optically active substances; thus it is impossible to be free from the temperature dependency or to obtain a temperature dependency which is contrary to the conventional one. Now, it has been reported that when an optically active substance having a helical twist right sense is mixed with that having a helical twist left sense in a definite proportion and the mixture is added to nematic liquid crystals, then it is possible to be free from the temperature dependency of the intrinsic helical pitch or to obtain a temperature dependency which is contrary to the conventional one (e.g. see U.S. Pat. No. 4,264,148, issued Apr. 28, 1981). In this case, however, an optically active substance having right twist and that having left twist are mixed so as to compensate these twists relative to one another to thereby obtain a definite intrinsic helical pitch; hence there is a case where the twistability ($P^{-1}$) becomes zero even in the vicinity of room temperature, depending on the mixing proportions, and above and below this temperature, the twisting senses are reverse to one another to thereby notably reduce the display quality of liquid crystal display elements using a liquid crystal composition of this type. Thus, only a considerably limited range of the mixing proportion will be employed. Further since the change of the intrinsic helical pitch is notable due to a slight difference of the mixing proportion, the temperature control of the intrinsic helical pitch is considerably difficult.

Further, since both a right twist optically active substance and a left twist one are added, one cannot help increasing the quantities thereof added, in order to obtain a desired helical pitch. Thus, the characteristics of the resulting nematic liquid crystal composition such as transition point, viscosity, threshold voltage $V_{th}$, etc. change considerably from the characteristics of the original nematic liquid crystals. Further, since optically active substances are expensive, the final liquid crystal composition is also expensive. On account of these drawbacks, the practical use of a liquid crystal composition having added such two kinds of right twist and left twist optically active substances has been notably restricted.

SUMMARY OF THE INVENTION

A first object of the present invention is to provide a liquid crystal composition having a temperature dependency of the twistability ($P^{-1}$) which is contrary to the conventional one and increases with temperature rise.

A second object of the present invention is to provide a nematic liquid crystal composition almost free from the temperature dependency of the twistability ($P^{-1}$).

A third object of the present invention is to provide a liquid crystal display element having inhibited reduction in display quality due to ambient temperature change and also having an improved angle of view, contrast, response speed, etc. in TN mode, SBE mode or DGH mode.

The present inventors have made extensive research on the temperature dependency of the intrinsic helical pitch of liquid crystal compositions induced by singly adding various optically active substances to nematic liquid crystals. As a result, the present inventors have found that so far known optically active substances reduce the reciprocal of helical pitch $P^{-1}$ of the resulting liquid crystal composition with temperature rise (that is, the temperature dependency is negative), whereas utterly contrarily to the above, there exist optically active substances which, when singly added to nematic liquid crystals, increase twistability $P^{-1}$ of the induced cholesteric phase in the resulting liquid crystal composition with temperature rise (that is, the temperature dependency is positive). Further the present inventors have also found that when an optically active substance which makes the temperature dependency of $P^{-1}$ positive is mixed with an optically active substance which has the same helical twist sense as that of the former substance and makes the temperature dependency negative, and the mixture is added to nematic liquid crystals, it is possible to optionally control the temperature dependency of the intrinsic helical pitch of the resulting liquid crystal composition.

The present invention in a first aspect resides in (1) a nematic liquid crystal composition which comprises (i) an optically active substance or a mixture of such substances which are the same in the helical twist sense to one another and which substance or mixture of substances make positive the temperature dependency of the twistability in terms of the reciprocal of the intrinsic helical pitch thereof, of the cholesteric phase induced when singly added to at least one member of nematic liquid crystals, and (ii) at least one member of nematic liquid crystals, to thereby notably increase the twistability with temperature rise.

The embodiments of the item (1) are shown in the following items (2) to (6):

(2) a nematic liquid crystal composition as an optically active substance according to the item (1), wherein said optically active substances are selected from the group consisting of compounds expressed by the formula (Ia), those expressed by the formula (Ib) and those expressed by the formula (Ic), and have the optically active

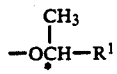

group or the

group:

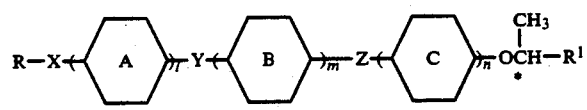

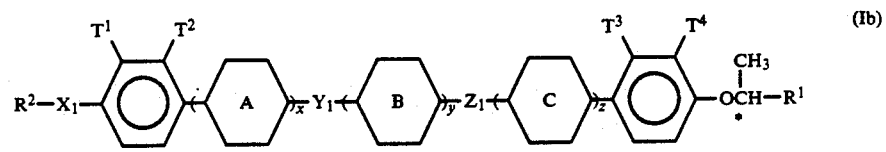

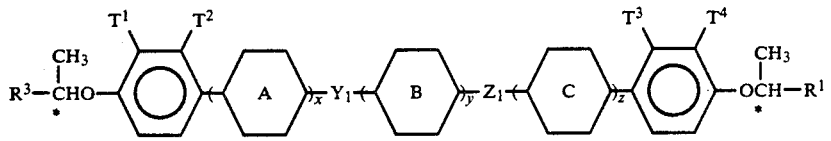

In the above formula (Ia),

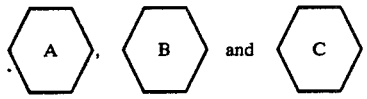

each independently represent benzene ring, cyclohexane ring, dioxane ring, pyrimidine ring or pyridine ring;
l and m each represent an integer of 0, 1 or 2;
n represents an integer of 1 or 2;
the total value of (l+m+n) is 1 to 4;
X represents a single bond,

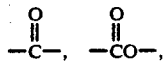

—CH$_2$— or —CH$_2$CH$_2$—;
Y represents a single bond when l=0;
Z represents a single bond when m=0;
Y and Z each independently represent

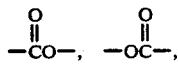

—CH$_2$O—, —OCH$_2$—, —CH$_2$CH$_2$—, —CH=N— or —N=CH— when l·m≠0;
R represents an alkyl group or an alkoxy group each of 1 to 15 carbon atoms or cyano group;
R$^1$ represents a linear chain alkyl group of 2 to 10 carbon atoms; and
X represents a single bond when R is cyano group.
In the above formula (Ib),

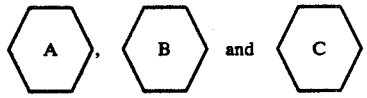

each independently represent benzene ring, cyclohexane ring, dioxane ring, pyrimidine ring or pyridine ring;
x and z each represent an integer of 0 or 1;
y represents an integer of 0, 1 or 2;
the total value of (x+y+z) is 0~2;
X$_1$ represents a single bond,

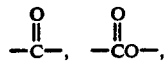

—CH$_2$O— or —CH$_2$CH$_2$—;
Y$_1$ represents a single bond when y=0, and Y$_1$ represents

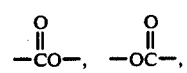

—CH$_2$O—, —OCH$_2$—, —CH$_2$CH$_2$—, —CH=N— or —N=CH— when y is 1 or 2;
Z$_1$ represents a single bond,

—CH$_2$O—, —OCH$_2$—, —CH$_2$CH$_2$—, —CH=N— or —N=CH—;
T$^1$, T$^2$, T$^3$ and T$^4$ each independently represent hydrogen atom, a halogen atom or cyano group;
R$^2$ represents an alkyl group or an alkoxy group each of 1 to 15 carbon atoms or cyano group or a halogen atom, and X$_1$ represents a single bond when R$^2$ is cyano group or a halogen atom; and
R$^1$ represents a linear chain alkyl group of 2 to 10 carbon atoms.
In the above formula (Ic),

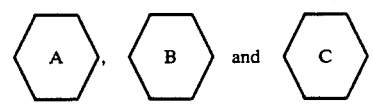

each independently represent benzene ring, cyclohexane ring, dioxane ring, pyrimidine ring or pyridine ring;
x and z each represent an integer of 0 or 1;
y represents an integer of 0, 1 or 2;
the total value of (x+y+z) is 0 to 2;
Y$_1$ represents a single bond when y=0, and Y$_1$ represents

—CH$_2$O—, —OCH$_2$—, —CH$_2$CH$_2$—, —CH=N— or —N=CH— when y is 1 or 2;
Z$_1$ represents a single bond,

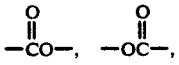

—CH$_2$O—, —OCH$_2$—, —CH$_2$CH$_2$—, —CH=N— or —N=CH—;
T$^1$, T$^2$, T$^3$ and T$^4$ each independently represent hydrogen atom, a halogen atom or cyano group; and
R$^1$ and R$^3$ each independently represent a linear chain alkyl group of 2 to 10 carbon atoms.

(3) A nematic liquid crystal composition according to the item (2) wherein said optically active substances selected from compounds expressed by the formula (Ia), compounds expressed by the formula (Ib) and compounds expressed by the formula (Ic) are contained in a quantity in the range of 0.05 to 10% by weight in said composition.

(4) A nematic liquid crystal composition according to the item (2) wherein said optically active substances are expressed by the formula (III)

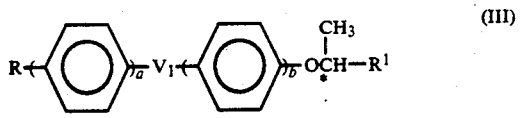

wherein a represents an integer of 0, 1 or 2; b represents an integer of 1 or 2; the value of (a+b) is 2 or 3; $V_1$ represents a single bond when a=0, and represents —COO—, —OCO—, —CH$_2$O—, —OCH$_2$— or —CH$_2$CH$_2$— when a is 1 or 2; and R and $R^1$ are as defined above.

(5) A nematic liquid crystal composition according to the item (2) wherein said optically active substances are expressed by the formula (IV)

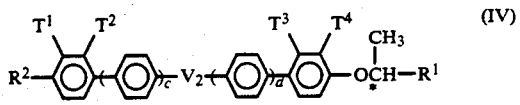

wherein c and d each represent an integer of 0 or 1; $V_2$ represents a single bond, —COO— or —OCO—; $T^1$, $T^2$, $T^3$ and $T^4$, each represent hydrogen atom, halogen atom or cyano group; and $R^1$ and $R^2$ each are as defined above.

(6) A nematic liquid crystal composition according to the item (2) wherein said optically active substances are expressed by the formula (V)

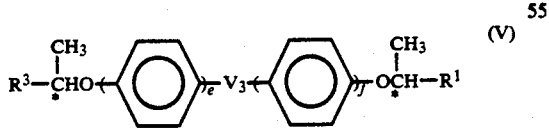

wherein e represents an integer of 0, 1 or 2; f represents an integer of 1 or 2; the value of (e+f) is 1 to 3; $V_3$ represents a single bond when e=0, and represents —COO— or —CH$_2$O— when e is 1 or 2; and $R^1$ and $R^3$ are as defined above.

The present invention in a second aspect resides in (7) a nematic liquid crystal composition which comprises (i) at least one member of optically active substances which make positive the temperature dependency of the twistability in terms of the reciprocal of the intrinsic helical pitch thereof, of the cholesteric phase induced when singly added to at least one member of nematic liquid crystals, (ii) at least one member of optically active substances which have the same helical twist sense as that of the former optically active substances and make negative the temperature dependency of the twistability of the induced cholesteric phase when singly added to at least one member of nematic liquid crystals, and (iii) at least one member of nematic liquid crystals.

The embodiments of the item (7) are shown in the following items (8) to (17):

(8) A nematic liquid crystal composition according to the item (7), wherein said optically active substances (i) which make positive the temperature dependency of the twistability of the cholesteric phase induced when singly added to at least one member of nematic liquid crystals are compounds selected from the group consisting of compounds expressed by the following formula (Ia), compounds expressed by the following formula (Ib) and compounds expressed by the following formula (Ic), and said optically active substances (ii) which have the same helical sense as that of the former optically active substances and which make negative the temperature dependency of the twistability of the cholesteric phase induced when singly added to at least one member of nematic liquid crystals are compounds expressed by the following formula (II):

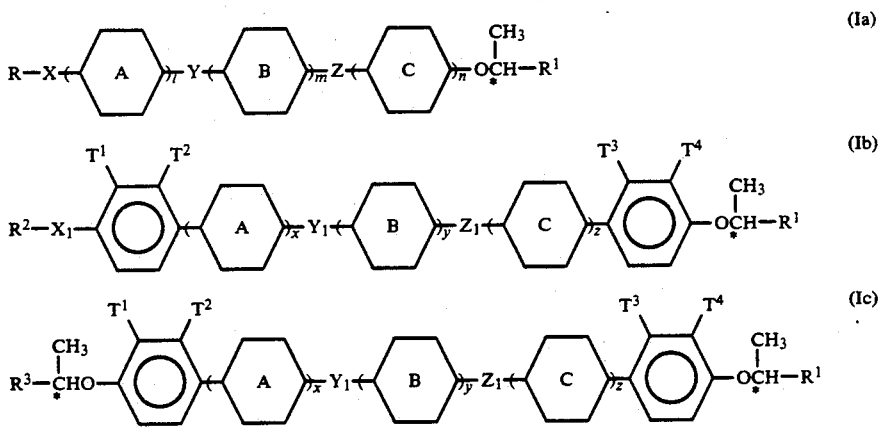

In the above formula (Ia),

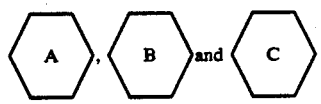

each independently represent benzene ring, cyclohexane ring, dioxane ring, pyrimidine ring or pyridine ring;
l and m each represent an integer of 0, 1 or 2;
n represents an integer of 1 or 2;
the value of (l+m+n) is 1 to 4;
X represents a single bond,

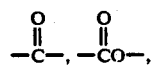

—CH$_2$— or —CH$_2$CH$_2$—;
Y represents a single bond when l=0, and Z represents a single bond when m=0, and Y and Z each independently represent —$\overset{O}{\underset{\|}{C}}$O—, —O$\overset{O}{\underset{\|}{C}}$—, —CH$_2$O—, —OCH$_2$—, —CH$_2$CH$_2$—, —CH=N— or —N=CH— when l·m≠0;
R represents an alkyl group or an alkoxy group each of 1 to 15 carbon atoms or cyano group;
R$^1$ represents a linear chain alkyl group of 2 to 10 carbon atoms; and
X represents a single bond when R is cyano group.

In the above formula (Ib),

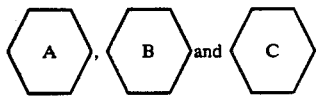

each independently represent benzene ring, cyclohexane ring, dioxane ring, pyrimidine ring or pyridine ring;
x and z each represent an integer of 0 or 1;
y represents an integer of 0, 1 or 2;
the value of (x+y+z) is 0 to 2;
X$_1$ represents a single bond, —$\overset{O}{\underset{\|}{C}}$—, —$\overset{O}{\underset{\|}{C}}$O—, —CH$_2$O or —CH$_2$CH$_2$—;
Y$_1$ represents a single bond when y=0 and represents —$\overset{O}{\underset{\|}{C}}$O—, —O$\overset{O}{\underset{\|}{C}}$—, —CH$_2$O—, —OCH$_2$—, —CH$_2$CH$_2$—, —CH=N— or —N=CH— when y is 1 or 2;
Z$_1$ represents a single bond, —$\overset{O}{\underset{\|}{C}}$O—, —O$\overset{O}{\underset{\|}{C}}$—, —CH$_2$O—, —OCH$_2$—, —CH$_2$CH$_2$—, —CH=N— or —N=CH—;
T$^1$, T$^2$, T$^3$ and T$^4$ each independently represent hydrogen atom, a halogen atom or cyano group;
R$^2$ represents an alkyl group or an alkoxy group each of 1 to 15 carbon atoms or cyano group or a halogen atom, and when R$^2$ is cyano group or a halogen atom, X$_1$ represents a single bond; and
R$^1$ represents a linear chain alkyl group of 2 to 10 carbon atoms.

In the above formula (Ic),

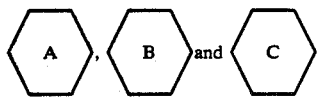

each independently represent benzene ring, cyclohexane ring, dioxane ring, pyrimidine ring or pyridine ring;
x and z each represent an integer of 0 or 1;
y represents an integer of 0, 1 or 2;
the value of (x+y+z) is 0 to 2;
Y$_1$ represents a single bond when y=0, and represents —$\overset{O}{\underset{\|}{C}}$O—, —O$\overset{O}{\underset{\|}{C}}$—, —CH$_2$O—, —OCH$_2$—, —CH$_2$CH$_2$—, —CH=N— or —N=CH— when y is 1 or 2;
Z$_1$ represents a single bond, —$\overset{O}{\underset{\|}{C}}$O—, —O$\overset{O}{\underset{\|}{C}}$—, —CH$_2$O—, —OCH$_2$—, —CH$_2$CH$_2$—, —CH=N— or —N=CH—;
T$^1$, T$^2$, T$^3$ and T$^4$ each independently represent hydrogen atom, a halogen atom or cyano group; and
R$^1$ and R$^3$ each independently represent a linear chain alkyl group of 2 to 10 carbon atoms.

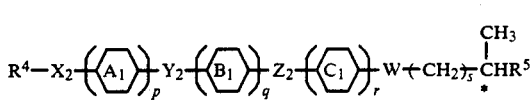

In the formula (II),

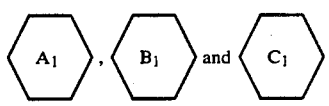

each independently represent benzene ring, cyclohexane ring, dioxane ring, pyrimidine ring or pyridine ring;
p and q each represent 0, 1 or 2;
r represents 1 or 2;
the value of (p+q+r) is 1 to 4;
s represents 0, 1, 2, 3 or 4;
X$_2$ represents —O—, —CO—, —COO—, —OCO—, —OCOO—, —OCH$_2$— or —OCH$_2$CH$_2$—;
Y$_2$ represents a single bond when p=0;
Z$_2$ represents a single bond when q=0;
Y$_2$ and Z$_2$ each independently represent —COO—, —OCO—, —CH$_2$O—, —OCH$_2$—, —CH$_2$CH$_2$—, —CH=N— or —N=CH— when p·q≠0;
W represents a single bond —COO— or —OCO— when s=0, and represents —O—, —COO— or —OCO— when s represents 1, 2, 3 or 4;
R$^4$ represents an alkyl group of 1 to 15 carbon atoms or cyano group;
R$^5$ represents a linear chain alkyl group of 2 to 10 carbon atoms; and
X$_2$ represents a single bond when R$^4$ is cyano group.

(9) A nematic liquid crystal composition according to the item (8) wherein optically active substances selected from the group consisting of compounds expressed by the formula (Ia), compounds expressed by the formula (Ib) and compound expressed by the formula (Ic), together with optically active substances expressed by the formula (II), are contained in a quantity of 0.05 to 10% by weight in the composition.

(10) A nematic liquid crystal composition according to the item (8) wherein said optically active substances which make positive the temperature dependency of the twistability are compounds expressed by the following formula (III) and said optically active substances which have the same helical twist sense as that of the former optically active substances and which make negative the temperature dependency of the twistability are compounds expressed by the following formula (VI):

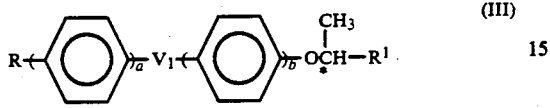

wherein
a represents an integer of 0, 1 or 2;
b represents an integer of 1 or 2;
the value of (a+b) is 2 or 3;
$V_1$ represents a single bond when a=0 and represents —COO—, —OCO—, —CH$_2$O, —OCH$_2$— or —CH$_2$CH$_2$— when a is 1 or 2;
R represents an alkyl group or an alkoxy group each of 1 to 15 carbon atoms or cyano group; and
$R^1$ represents a linear chain alkyl group of 2 to 10 carbon atoms.

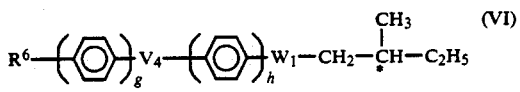

wherein
g represents 0, 1 or 2;
h represents 1 or 2;
the value of (g+h) is 1 to 3;
$V_4$ represents a single bond when g=0 and represents —COO—, —OCO—, —CH$_2$O— or —OCH$_2$— when g is 1 or 2;
$W_1$ represents a single bond, —O— or —COO—; and
$R^6$ represents an alkyl group or an alkoxy group each of 1 to 15 carbon atoms or cyano group.

(11) A nematic liquid crystal composition according to the item (8) wherein said optically active substances which make positive the temperature dependency of the twistability are compounds expressed by the following formula (III) and said optically active substances which have the same helical twist sense as that of the former optically active substances and which make negative the temperature dependency of the twistability are compounds expressed by the following formula (VII):

wherein
b represents an integer of 1 or 2;
the value of (a+b) is 2 or 3;
$V_1$ represents a single bond when a=0 and represents —COO—, —OCO—, —CH$_2$O—, —OCH$_2$— or —CH$_2$CH$_2$— when a is 1 or 2;
R represents an alkyl group or an alkoxy group each of 1 to 15 carbon atoms or cyano group; and $R^1$ represents a linear chain alkyl group of 2 to 10 carbon atoms.

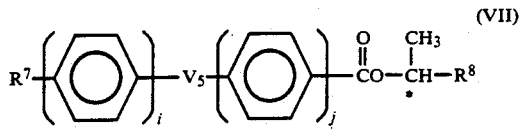

wherein
i represents 0, 1 or 2;
j represents 1 or 2;
the value of (i+j) is 1 to 3;
$V_5$ represents a single bond when i=0 and represents —COO—, —OCO—, —CH$_2$O— or —OCH$_2$— when i is 1 or 2;
$R^7$ represents an alkyl group or an alkoxy group each of 1 to 15 carbon atoms; and
$R^8$ represents a linear chain alkyl group of 2 to 10 carbon atoms.

(12) A nematic liquid crystal composition according to the item (8) wherein said optically active substances which make positive the temperature dependency of the twistability are compounds expressed by the following formula (IV) and said optically active substances which have the same helical twist sense as that of the former optically active substances and which make negative the temperature dependency of the twistability are compounds expressed by the following formula (VI):

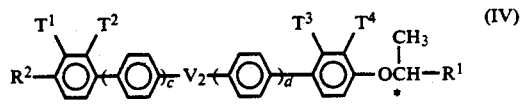

wherein
c and d each represent an integer of 0 or 1;
$V_2$ represents a single bond, —COO— or —OCO—;
$T^1$, $T^2$, $T^3$ and $T^4$ each represent hydrogen atom, halogen atom or cyano group;
$R^1$ represents a linear chain alkyl group of 2 to 10 carbon atoms; and
$R^2$ represents an alkyl group or an alkoxy group each of 1 to 15 carbon atoms, cyano group or halogen atom.

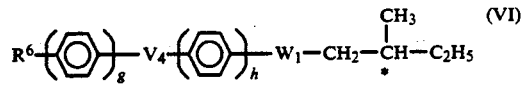

wherein
g represents 0, 1 or 2;
h represents 1 or 2;
the value of (g+h) is 1 to 3;
$V_4$ represents a single bond when g=0 and represents —COO—, —OCO—, —CH$_2$O— or —OCH$_2$— when g is 1 or 2;
$W_1$ represents a single bond, —O— or —COO—; and
$R^6$ represents an alkyl group or an alkoxy group each of 1 to 15 carbon atoms or cyano group.

(13) A nematic liquid crystal composition according to the item (8) wherein said optically active substances which make positive the temperature dependency of the twistability are compounds expressed by the following formula (IV) and said optically active substances which have the same helical twist sense as that of the former optically active substances and make negative the temperature dependency of the twistability are compounds expressed by the following formula (VII):

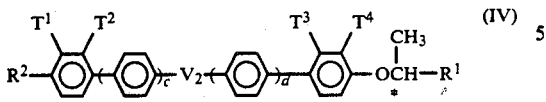 (IV)

wherein
c and d each represent an integer of 0 or 1;
$V_2$ represents a single bond, —COO— or —OCO—;
$T^1$, $T^2$, $T^3$ and $T^4$ each represent hydrogen atom, halogen atom or cyano group;
$R^1$ represents a linear chain alkyl group of 2 to 10 carbon atoms; and
$R^2$ represents an alkyl group or an alkoxy group each of 1 to 15 carbon atoms, cyano group or halogen atom.

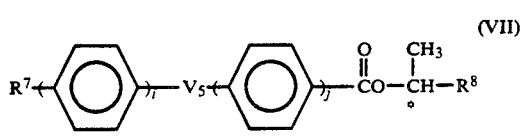 (VII)

wherein
i represents 0, 1 or 2;
j represents 1 or 2;
the value of (i+j) is 1 to 3;
$V_5$ represents a single bond when i=0 and represents —COO—, —OCO—, —CH$_2$O—, or —OCH$_2$— when i is 1 or 2;
$R^7$ represents an alkyl group or an alkoxy group each of 1 to 15 carbon atoms; and
$R^8$ represents a linear chain alkyl group of 2 to 10 carbon atoms.

(14) A nematic liquid crystal composition according to the item (8) wherein said optically active substances which make positive the temperature dependency of the twistability are compounds expressed by the following formula (V) and said optically active substances which have the same helical twist sense as that of the former optically active substances and which make negative the temperature dependency of the twistability are compounds expressed by the following formula (VI):

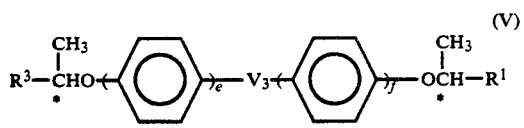 (V)

wherein
e represents an integer of 0, 1 or 2;
f represents an integer of 1 or 2;
the value of (e+f) is 1 to 3;
$V_3$ represents a single bond when e=0 and represents —COO— or —CH$_2$O— when e is 1 or 2; and
$R^1$ and $R^3$ each independently represent a linear chain alkyl group of 2 to 10 carbon atoms.

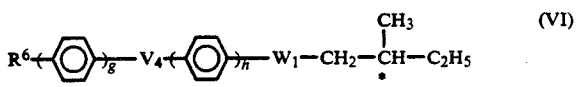 (VI)

wherein
g represents 0, 1 or 2;

h represents 1 or 2;
the value of (g+h) is 1 to 3;
$V_4$ represents a single bond when g=0 and represents —COO—, —OCO—, —CH$_2$O— or —OCH$_2$— when g is 1 or 2;
$W_1$ represents a single bond, —O—, or —COO—; and
$R^6$ represents an alkyl group or an alkoxy group each of 1 to 15 carbon atoms or cyano group.

(15) A nematic liquid crystal composition according to the item (8) wherein said optically active substances which make positive the temperature dependency of the twistability are compounds expressed by the following formula (V) and said optically active substances which have the same helical twist sense as that of the former optically active substances and which make negative the temperature dependency of the twistability are compounds expressed by the following formula (VII):

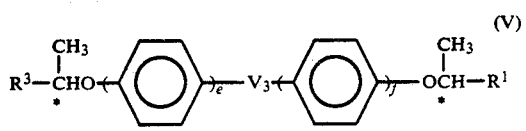 (V)

wherein
e represents an integer of 0, 1 or 2;
f represents an integer of 1 or 2;
the value of (e+f) is 1 to 3;
$V_3$ represents a single bond when e=0 and represents —COO— or —CH$_2$O— when e is 1 or 2; and
$R^1$ and $R^3$ each independently represents a linear chain alkyl group of 2 to 10 carbon atoms.

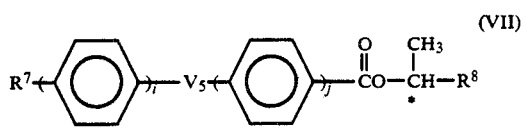 (VII)

wherein
i represents 0, 1 or 2;
j represents 1 or 2;
the value of (i+j) is 1 to 3;
$V_5$ represents a single bond when i=0 and represents —COO—, —OCO—, —CH$_2$O or —OCH$_2$— when j is 1 or 2;
$R^7$ represents an alkyl group or an alkoxy group each of 1 to 15 carbon atoms; and
$R^8$ represents a linear chain alkyl group of 2 to 18 carbon atoms.

(16) A nematic liquid crystal composition according to the item (8) wherein said optically active substances are selected so that the twistability of the induced cholesteric phase can be constant irrespective of temperature change in a definite temperature range.

(17) A nematic liquid crystal composition according to claim 8 wherein said optically active substances are selected so that the temperature dependency of the twistability of the induced cholesteric phase can have a desired value in a definite temperature range.

The present invention in a third aspect resides in the following items (18) and (19):

(18) A liquid crystal display element characterized by using a nematic liquid crystal composition which comprises (i) at least one member of optically active substances which are the same in the helical twist sense to one another and make positive the temperature dependency of the twistability in terms of the reciprocal of the intrinsic helical pitch thereof, of the cholesteric phase induced when singly added to at least one member of nematic liquid crystals, and (ii) at least one member of nematic liquid crystals, to thereby notably increase the twistability with temperature rise.

(19) A liquid crystal display element characterized by using a nematic liquid crystal composition which comprises (i) at least one member of optically active substances which make positive the temperature dependency of the twistability in terms of the reciprocal of the intrinsic helical pitch thereof, of the cholesteric phase induced when singly added to at least one member of nematic liquid crystals, (ii) at least one member of optically active substances which have the same helical twist sense as that of the former optically active substances and make negative the temperature dependency of the twistability of the cholesteric phase induced when singly added to at least one member of nematic liquid crystals, and (iii) at least one member of nematic liquid crystals.

BRIEF DESCRIPTION OF THE DRAWINGS

FIGS. 11, 13, 14, 15, 16, 18, 19, 20 and 21 respectively show a chart illustrating the normalized value of temperature dependency of the twistability between 20° C. and 70° C.

DETAILED DESCRIPTION OF PREFERRED EMBODIMENTS

The present invention will be described referring to examples.

Figure 4:
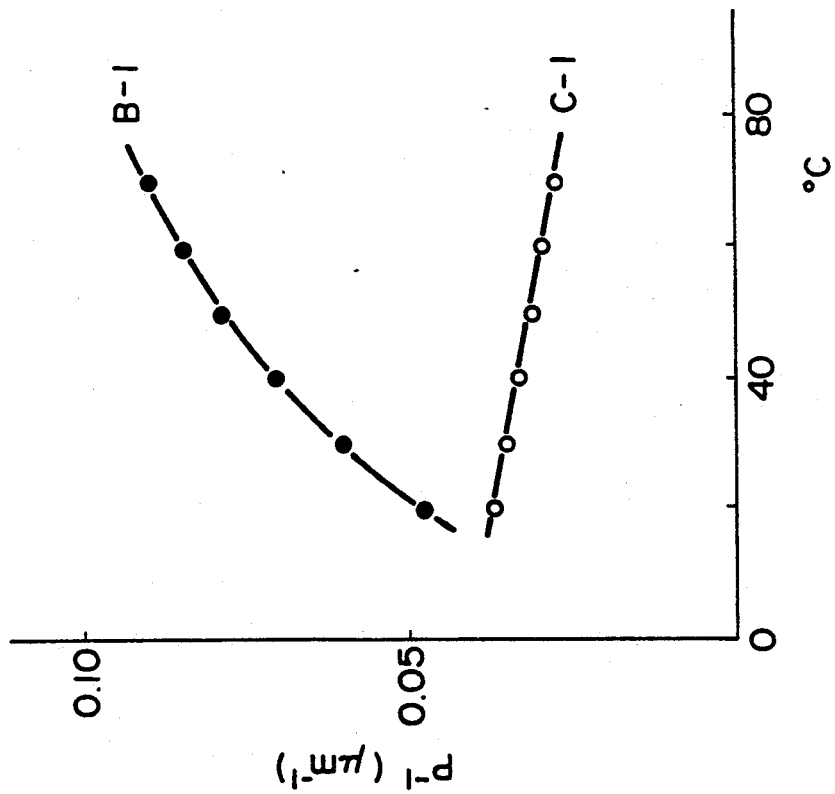

In FIG. 4 is shown the temperature dependency of twistability ($P^{-1}$) in the case where an optically active substance B-1 of the formula

Figure 2:
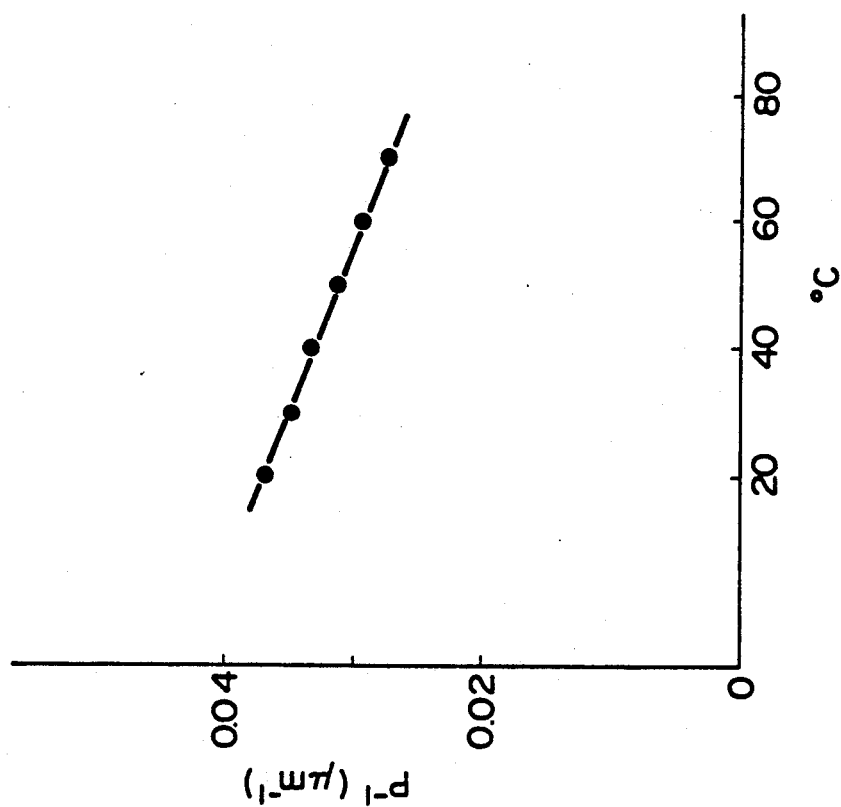
FIGS. 2, 4, 5, 6 and 12 respectively show a chart illustrating the temperature dependency of the twistability.
Figure 1:
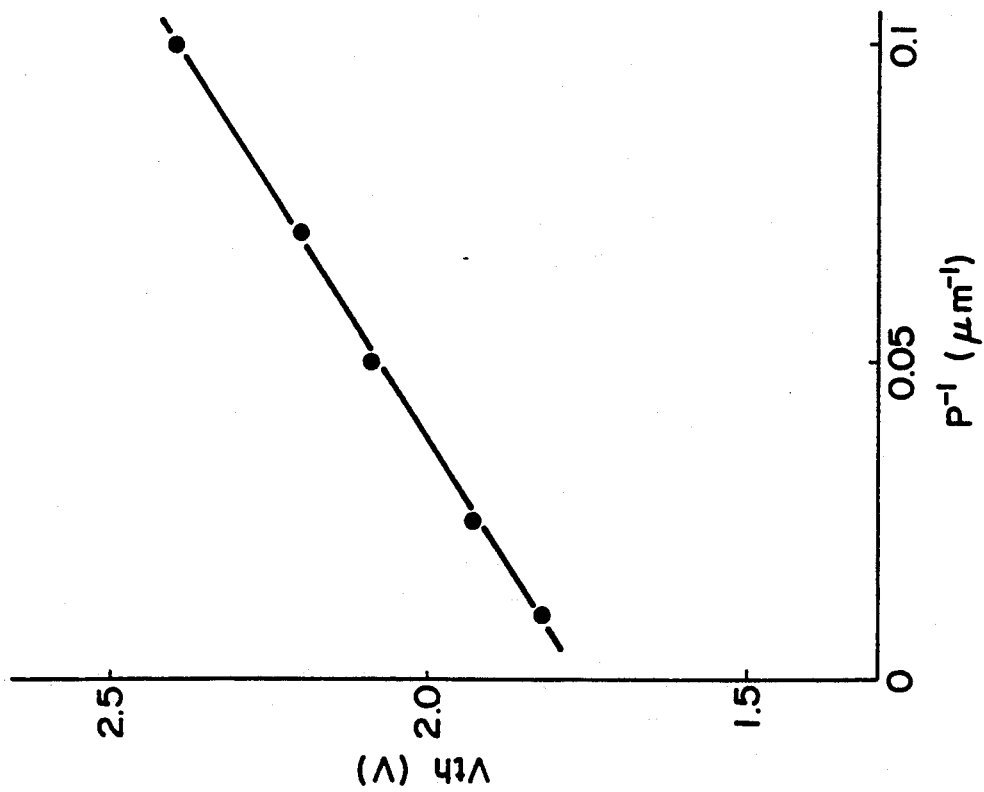
FIG. 1 shows a chart illustrating the twistability dependency of the threshold voltage.

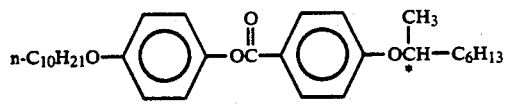

disclosed in Japanese patent application laid-open No. Sho 61/43 (1986), which substance is obtained using R(—)-2-octanol as a starting raw material and has a right helical twist sense is added to the aforementioned nematic liquid crystal composition A. For reference, the effect of the optically active substance C-1 shown in FIG. 2 is also shown therein. As seen from FIG. 4, the value of $P^{-1}$ in the case where the optically active substance B-1 is added increases with temperature rise, and exhibits a contrary tendency to that of a monotonic reduction in the case of addition of the compound C-1.

In general, as a parameter for comparing the temperature dependency of the twistability of a liquid crystal material in the temperature range between $t_1$ and $t_2$ will be employed the normalized value of $\Delta P^{-1}(t_1-t_2)$ expressed by the following equation specifying the above temperature dependency:

$$\Delta P^{-1}(t_1 \sim t_2) = \frac{2[P^{-1}(t_1) - P^{-1}(t^2)]}{P^{-1}(t_1) + P^{-1}(t^2)} \times \frac{100}{t_1 - t_2} \quad (4)$$

wherein $P^{-1}(t)$ refers to the value of a twistability at a temperature of t° C. These two nematic liquid crystal compositions were compared referring to the normalized values of the temperature dependency $\Delta P^{-1}(20\sim40)$ of the twistablility specified by the equation (4). As a result, the value of $\Delta P^{-1}(20\sim40)$ of the composition having the compound B-1 added as an optically active substance was 1.93, whereas that of the composition having the compound C-1 was $-0.48$.

Figure 3:
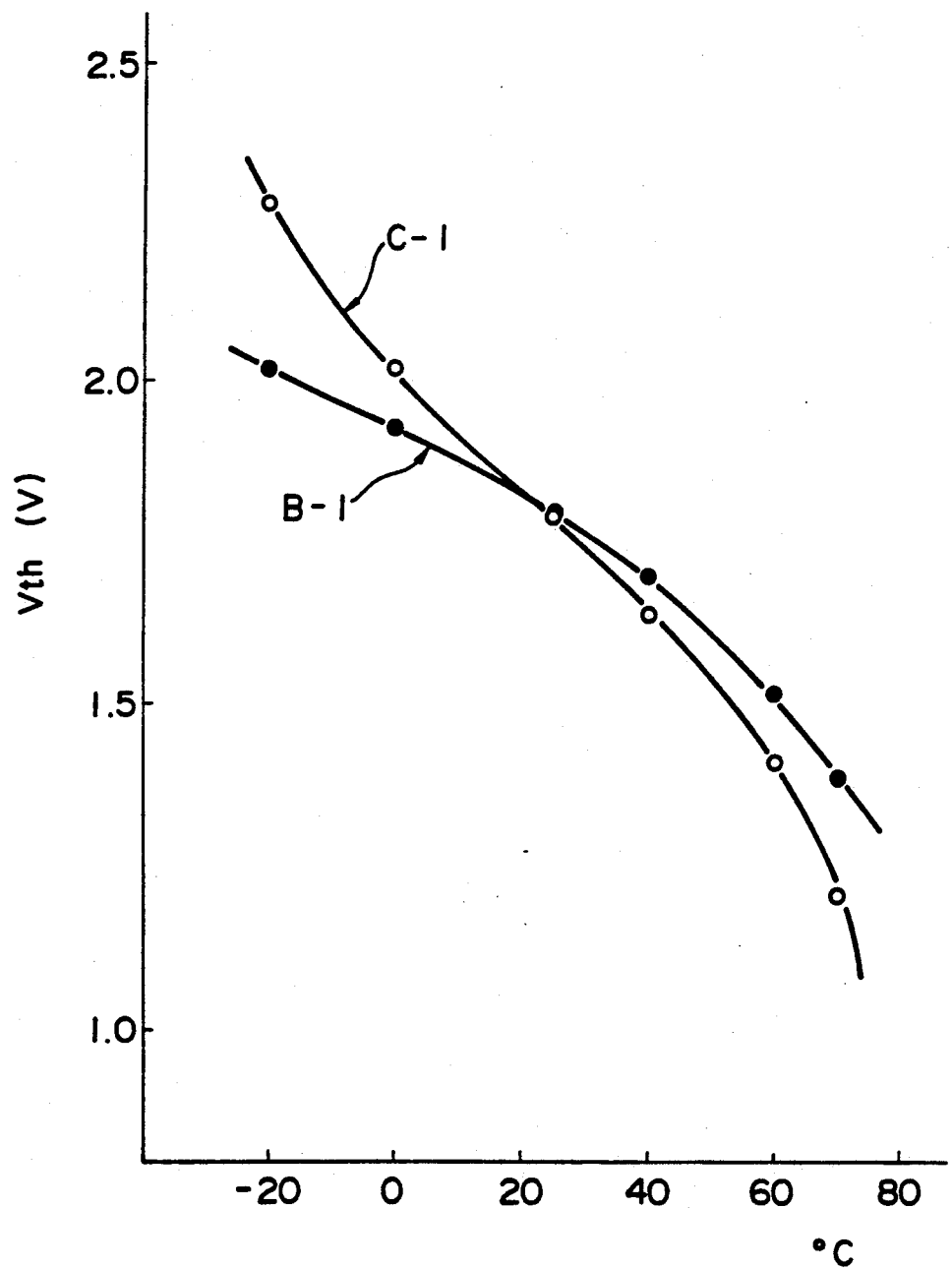
FIGS. 3, 7, 8, 9, 10 and 17 respectively show a chart illustrating the temperature dependency of the threshold voltage.

Further, a liquid crystal composition N and a liquid crystal composition C were respectively prepared by adding the compound B-1 (one part by weight) to the above liquid crystal composition (A) (100 parts by weight) and adding the compound C-1 (0.1 part by weight) to the composition (A) (100 parts by weight), and the resulting compositions were respectively sealed in a TN cell having a definite distance between the electrodes to compare the temperature dependencies of the threshold voltages ($V_{th}$). The results are shown in FIG. 3. As seen from the above example, the liquid crystal composition of the present invention containing the optically active substance B-1 has an improved temperature dependency of $V_{th}$, and in particular, the reduction of $V_{th}$ is small in the high temperature region of nematic phase temperature range.

As an example wherein two optically active substances each having an opposite helical twist sense to one another were added, a nematic liquid crystal composition M was prepared by adding the optically active substance C-1 having a right helical twist (2.0 parts by weight) and an optically active compound C-2 expressed by the formula

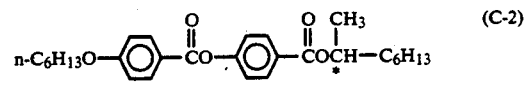

and having a left helical twist (1.5 part by weight) together to the above liquid crystal composition (A) (100 parts by weight), and the characteristics of this composition M were compared with those of the above liquid crystal composition N. The results are shown in Table 1. For reference, the characteristics of the nematic liquid compositions A and C are also shown therein.

TABLE 1

| | NI point (°C.) | Viscosity at 20° C. (cp) | $\Delta P^{-1}$ (20~40) | $\Delta V_{th}/\Delta t$ (0~40)* |
|---|---|---|---|---|
| Composition M | 70.2 | 27.8 | 1.49 | $-7.3$ |
| Composition N | 71.5 | 25.6 | 1.93 | $-6.0$ |
| Composition C | 71.8 | 25.8 | $-0.48$ | $-9.3$ |
| Composition A | 72.4 | 25.2 | | |

*$\Delta V_{th}/\Delta t$ refers to a parameter expressing the temperature dependency of threshold voltage defined in the equation (5) of Example 1 described later.

As seen from Table 1, since the composition N has a small quantity of the optically active substance added, its upper limit temperature (N-I point) of the nematic phase is not reduced so much from that of the original composition A, and also the viscosity rise is restricted to a small value. On the other hand, since the composition M has a large quantity of the optically active substance added, its N-I point lowers by 2° C. or more, and also its viscosity rise is much higher than that of the composition N. Further, in comparison of the temperature dependency of the threshold voltage, it is seen that the compositions N and M each having a positive $\Delta P^{-1}$ are smaller in $|\Delta V_{th}/\Delta t|$ as compared with the composition C having a negative $\Delta P^{-1}$. Further, in comparison of the composition N with the composition M, declination in the $\Delta V_{th}/\Delta t$ of the composition N is smaller than that of the composition M.

As described above, the composition of the present invention is collectively superior as a nematic liquid crystal composition having a positive temperature dependency of the twistability.

Examples of the optically active substances which are preferred as the component of the liquid crystal composition of the present invention are compounds expressed by the above-mentioned formulas (III)–(V). These are characterized by having an optically active group of

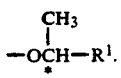

As to the structure of optically active groups, there are some kinds, and as to well-known

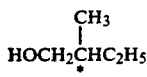

among raw material alcohols for introducing optically active groups, only the one having an absolute configuration of sinister type (S type) is existent in the natural world, and there has still been no example of its optical resolution; hence in the case of derivatives of such an alcohol, there is little room to choose those of right twist and left twist. Whereas, in the case of

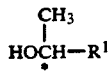

as the raw material for the optically active substances constituting a component of the composition of the present invention, the optical resolution thereof is easy and two kinds of optical isomers having an absolute configuration of S type and that of rectus type (R type), respectively are obtained; hence the freeness of choice in the form of optically active substances is large. In other words, two kinds of compounds having all the same structural formula but being different only in the steric configuration of the optically active group are produced to thereby obtain two kinds of optically active substances having all the same characteristics but having right and left twist senses, respectively. Further, adequate, separate use of such two kinds of optically active substances brings about an advantage that two kinds of compositions having all the same characteristics but having right and left twist senses, respectively are obtained.

Figure 5:
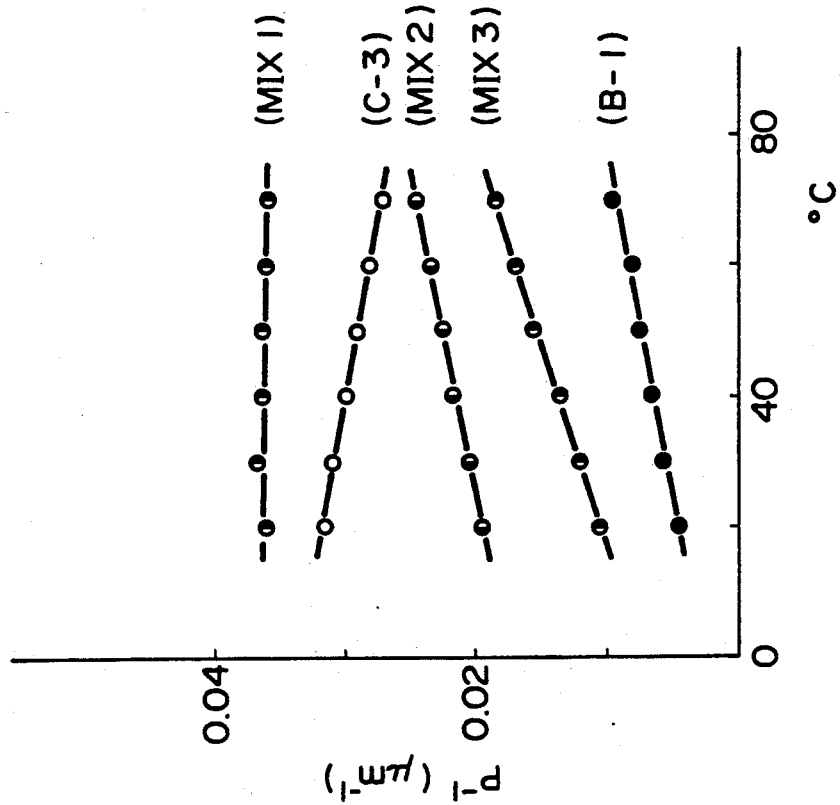

Next, the above-mentioned optically active substance B-1 (0.43 wt. %) and an optically active substance expressed by the following formula C-3 (0.57 wt. %):

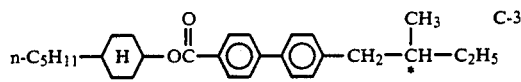

were mixed with the above-mentioned nematic liquid crystal composition (A). The temperature dependency of the twistability ($P^{-1}$) of the resulting liquid crystal composition is shown in FIG. 5. In FIG. 5, (Mix 1) shows the temperature dependency of the twistability ($P^{-1}$) in the case where optically active substances B-1 and C-3 were mixed and added to the composition (A), (B-1) shows that in the case where B-1 alone (0.43 wt. %) was added to the composition, and (C-3) shows that in the case where the compound C-3 alone (0.57 wt. %) was added thereto. As seen from FIG. 5, there is almost no change in $P^{-1}$ depending on temperature in the case of (Mix 1).

Further, the optically active substance B-1 (0.8 wt. %) and the optically active substance C-3 (0.2 wt. %) were added together to the nematic liquid crystal composition (A). The temperature dependency of the twistability ($P^{-1}$) of the resulting composition is shown as (Mix 2) of FIG. 5. Further, the case where the optically active substance B-1 alone (1.0 wt. %) was added is shown as (Mix 3) of FIG. 5.

In the cases of (Mix 2) and (Mix 3), it is seen that the twistability ($P^{-1}$) steeply increases with temperature rise. Further, the larger the proportion of B-1, the steeper the change in the twistability ($P^{-1}$). This indicates that by varying the mixing proportions of B-1 and C-3, it is possible to continuously and optionally control the temperature dependency of the twistability ($P^{-1}$) from its nearly constant state up to its steeply ascending state with temperature rise.

Further, the following optically active substance B-2 having a left helical twist sense, obtained by using as its starting raw material, S(+)-2-octanol disclosed in Japanese patent application laid-open No. Sho 61-43 (1986) (0.48 wt. %):

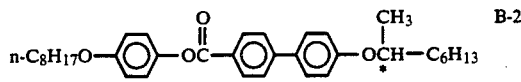

and the following optically active substance C-4 (0.52 wt. %):

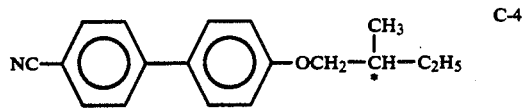

were mixed and added to the above nematic liquid crystal composition (A). The temperature dependency of the twistability ($P^{-1}$) of the resulting composition is shown in FIG. 6.

Figure 6:
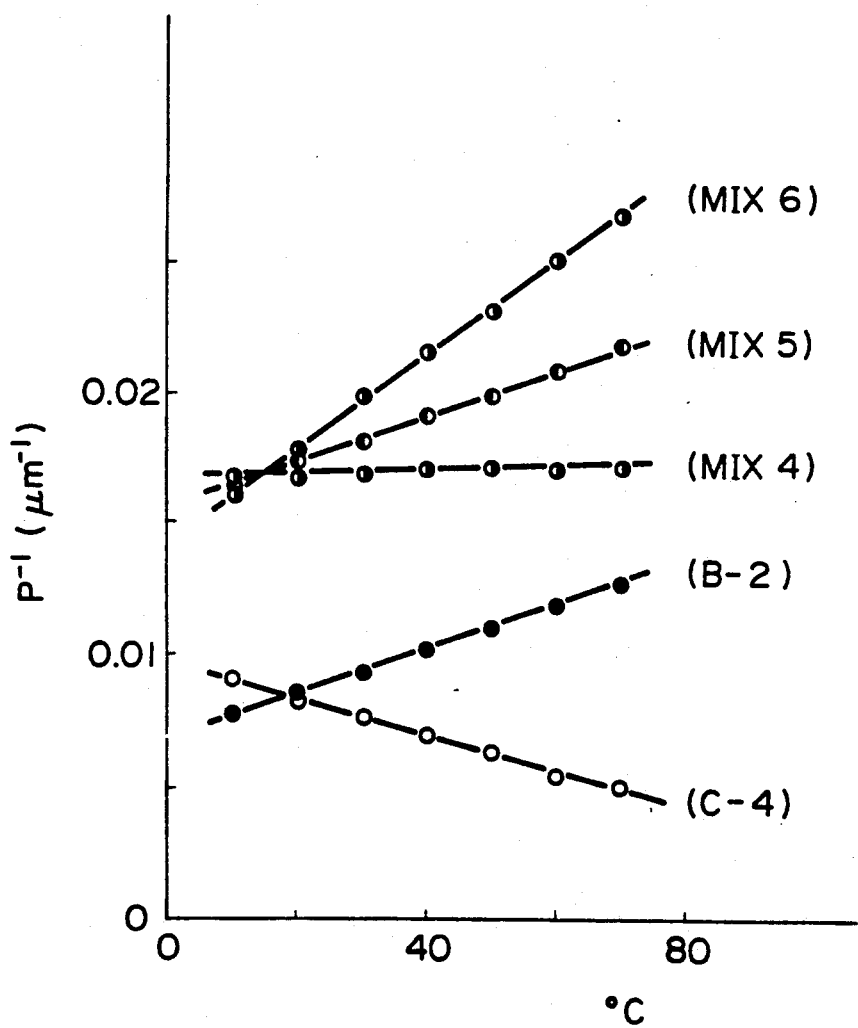

In FIG. 6, (Mix 4) shows the case where the optically active substances B-2 (0.48 wt. %) and C-4 (0.52 wt. %) were mixed and added; (B-2) shows the case where the compound B-2 alone (0.48 wt. %) was added; and (C-4) shows the case where the compound C-4 alone (0.52 wt. %) was added; thus (Mix 4) has still almost no change in $P^{-1}$ depending on temperature.

Further, the optically active substances B-2 (0.8 wt. %) and C-4 (0.2 wt. %) were mixed and added to the nematic liquid crystal composition (A). The temperature dependency of the twistability ($P^{-1}$) of the resulting composition is shown as (Mix 5) of FIG. 6. Further the case where the optically active substance B-2 alone (1.0 wt. %) was added is shown as (Mix 6) of FIG. 6.

In comparison of (Mix 5) with (Mix 6), the twistability ($P^{-1}$) steeply increases with temperature rise, and as the proportion of B-2 increases, change in the twistability ($P^{-1}$) becomes steep. This still indicates that by varying the mixing proportions of B-2 and C-4, it is possible to continuously and optionally control the temperature dependency of the twistability ($P^{-1}$) from its almost constant state up to a steeply ascending state with temperature rise.

As seen from the foregoing, if an optically active substance having a terminal group,

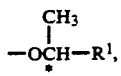

as shown in the general formula (Ia), the general formula (Ib) or the general formula (Ic) is used, either even in the case where the substance is added together with another optically active substance having a larger twistability ($P^{-1}$) at room temperature and the same helical twist sense (see FIG. 5), or contrarily even in the case where the substance is added together with another optically active substance having a smaller twistability ($P^{-1}$) at room temperature and the same helical twist sense (see FIG. 6), it is possible to optionally control the change in the intrinsic helical pitch depending on temperature change, of the resulting compositions. More details will be described later in Examples).

As the compounds expressed by the above general formulas (Ia), (Ib) and (Ic) among the optically active substances used as a component constituting the liquid crystal composition of the present invention, compounds expressed by the above formulas (III), (IV) and (V) and having a 1-methyl-alkyloxy group as an optically active group are preferred. Further, as the compounds expressed by the above formula (II) as the other optically active substances, compounds expressed by the above formulas (VI) and (VII) are suitable.

These compounds can be prepared for example as follows:

(1) Compounds of the formula (III) wherein $V_1$ represents —OCO— may be prepared according to the following scheme 1 (see Japanese patent application laid-open No. Sho 61-43):

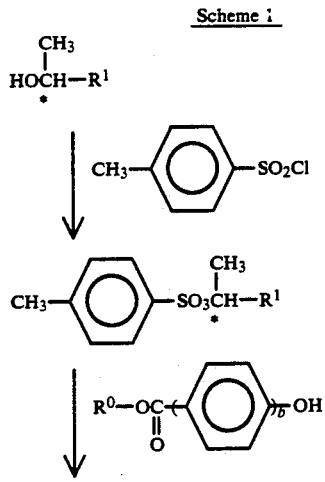

Scheme 1

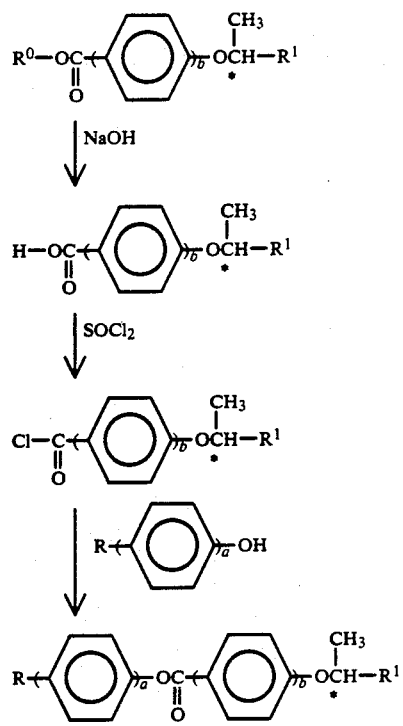

(2) Compounds of the formula (III) wherein $V_1$ represents —COO— may —COO— may be prepared according to the following scheme 2:

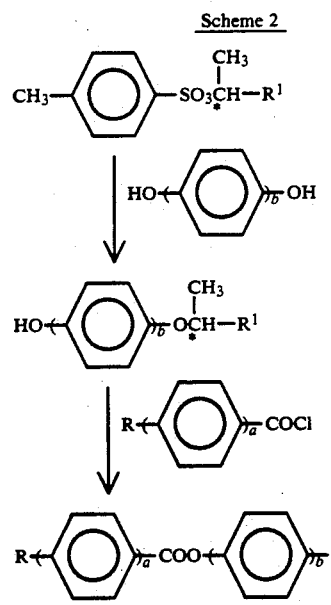

(3) Compounds of the formula (III) wherein $V_1$ represents —CH$_2$O— or —OCH$_2$— may be prepared according to the process disclosed in Japanese patent application laid-open No. Sho 61-63633.

(4) Compounds of the formula (IV) wherein $V_2$ represents —COO—; d represents zero; $T^1$, $T^2$ and $T^3$ each represent hydrogen atom; and $T^4$ represents a halogen atom may be prepared according to the following scheme 3.

Further, compounds of the formula (IV) wherein $V_2$ represents —COO—; either one of $T^1$ or $T^2$ represents a halogen atom and the other, $T^3$ and $T^4$ each represent hydrogen atom may be prepared according to the following scheme 4 (Japanese patent application No. Sho 61-51512, not yet laid-open).

Scheme 3

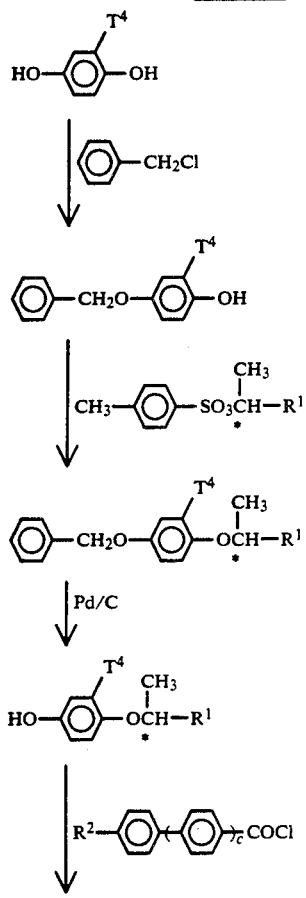

Scheme 4

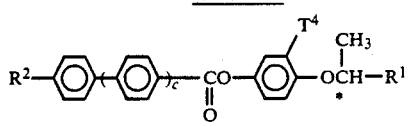

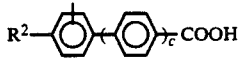

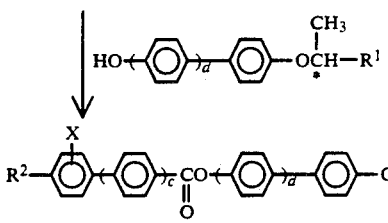

(5) Compounds of the formula (V) wherein $V_3$ represents —COO— may be prepared according to the following scheme 5:

Scheme 5

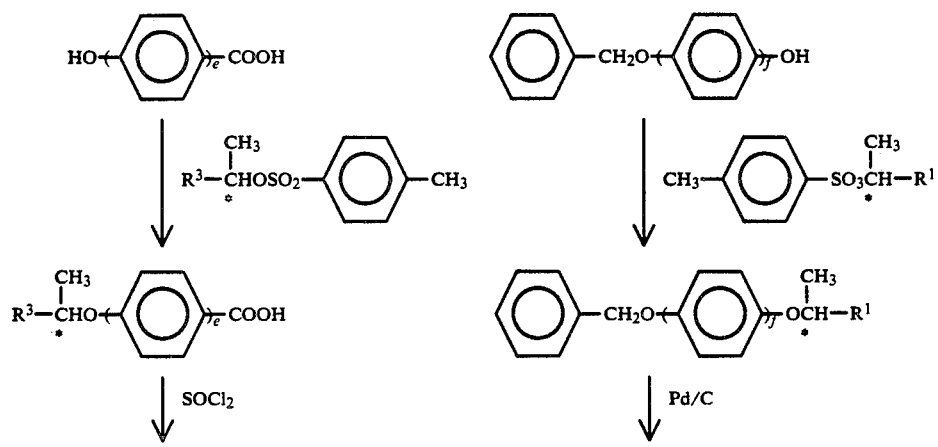

-continued
Scheme 5

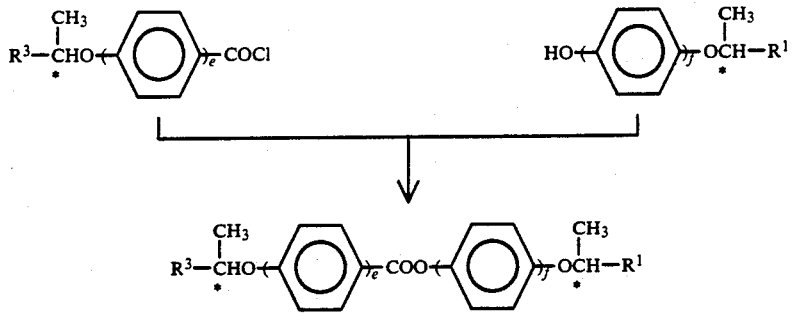

(6) Compounds of the formula (V) wherein e=0, f=2 and $V_3$ represents a single bond may be prepared according to the following scheme 6:

Scheme 6

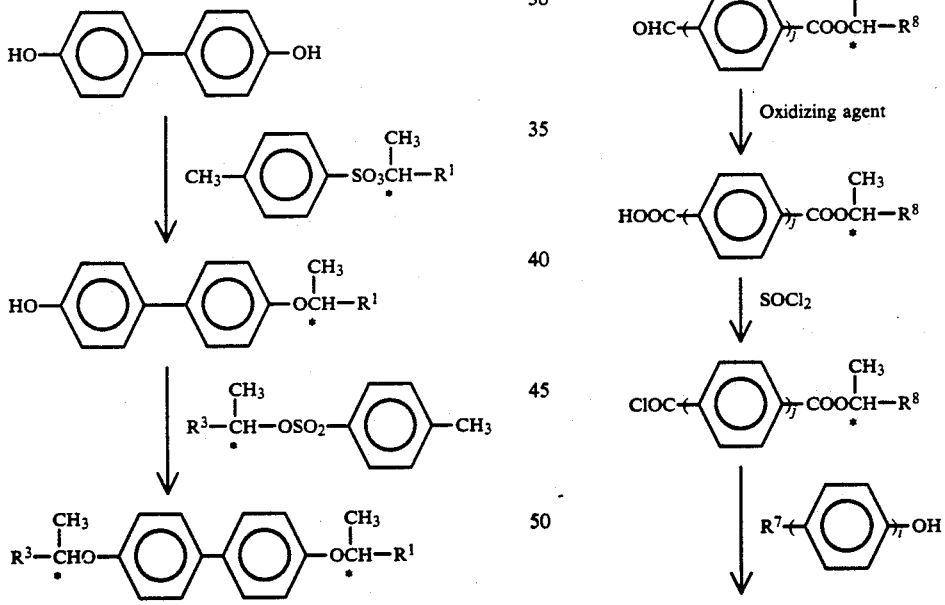

(7) Compounds of the formula (VII) wherein $V_5$ represents —OCO— may be prepared according to the process disclosed in Japanese patent application laid-open No. Sho 60-149548/1985 (scheme 7):

Scheme 7

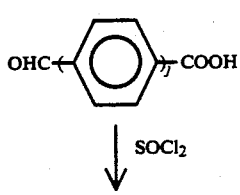

-continued
Scheme 7

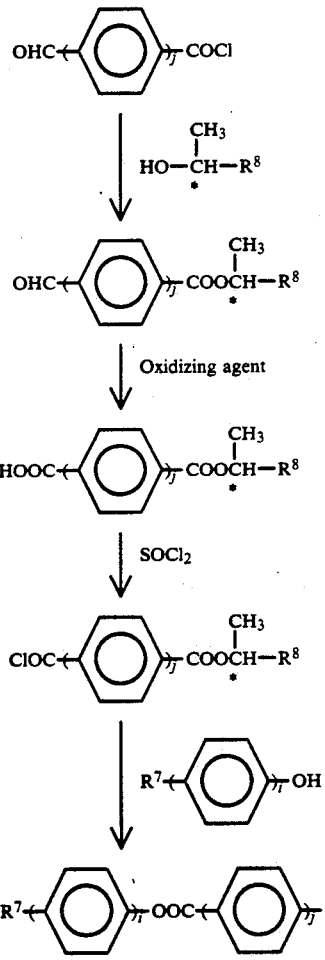

Compounds of the formula (VI) wherein $V_4$ represents —OCO— and $W_1$ represents —COO— may be prepared using an optically active alcohol

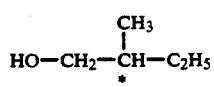

in the same manner as in the preparation of the scheme 7.

Certain compounds expressed by the formula (VI) or (VII) are commercially available. Some of these are illustrated in the following Table 2.

formula (III) with those expressed by the formula (VII) and adjusting the temperature dependency of $P^{-1}$ of the liquid crystal composition, it is possible to easily obtain two kinds of nematic compositions being different only in the helical twist sense but being the same in the other characteristics.

TABLE 2

| Producer & Trade Designation | | Structural formula |
|---|---|---|
| BDH Chemicals | CB-15 | $NC-\phi-\phi-CH_2-\overset{*}{C}H(CH_3)-C_2H_5$ |
| BDH Chemicals | C-15 | $NC-\phi-\phi-OCH_2-\overset{*}{C}H(CH_3)-C_2H_5$ |
| Merck & Co. | S 1082 | $C_6H_{13}O-\phi-COO-\phi-CO-CH_2-\overset{*}{C}H(CH_3)-C_2H_5$ |
| Merck & Co. | S 811 | $C_6H_{13}O-\phi-COO-\phi-CO-\overset{*}{C}H(CH_3)-C_6H_{13}$ |
| Chisso Corp. | CM-19 | $C_5H_{11}-\phi-\phi-COO-CH_2-\overset{*}{C}H(CH_3)-C_2H_5$ |
| Chisso Corp. | CM-20 | $C_5H_{11}-Cy-OCO-\phi-\phi-CH_2-\overset{*}{C}H(CH_3)-C_2H_5$ |
| Chisso Corp. | ER-M | $NC-\phi-OCO-\phi-OCH_2-\overset{*}{C}H(CH_3)-C_2H_5$ |

In addition, from

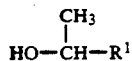

as a raw material for optically active substances expressed by the formula (III) and being a component constituting the composition of the present invention are, also prepared compounds expressed by the above formula (VII). Such compounds are characterized by having an optically active group of

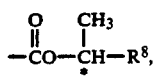

and the temperature depend ($\Delta P^{-1}$) of the twistability of the cholesteric phase induced when singly added to nematic liquid crystals is negative.

Among compounds expressed by the formula (III) or the formula (VII), two kinds of isomers having the same structure but being different only in the steric configuration of the optically active group are existent. These isomers are opposite in the helical twist sense to one another, but other characteristics thereof are same. By combining optically active substances expressed by the formula (III) with those expressed by the formula (VII) and adjusting the temperature dependency of $P^{-1}$ of the liquid crystal composition, it is possible to easily obtain two kinds of nematic compositions being different only in the helical twist sense but being the same in the other characteristics.

For example, it is also possible to combine an optically active substance having a group

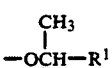

and having a left twist sense, obtained using S(+)-2-octanol as a starting raw material, with an optically active substance having a group

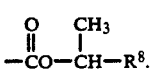

and having a left twist sense, obtained using S(+)-2-octanol as a starting raw material. Further, it is also possible to combine an optically active substance having a group

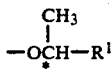

and having a right twist sense, obtained using R(—)-2-octanol as a starting raw material, with an optically active substance having a group

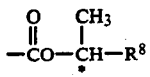

and having a right twist sense, obtained using R(—)-2-octanol as a starting raw material.

What is important in the present invention is that when a compound selected from the group consisting of compounds expressed by the formulas (Ia), (Ib) and (Ic) is combined with a compound expressed by the formula (II) and the mixture is added to a nematic liquid crystal composition to thereby control the temperature dependency of the twistability, the respective helical twist senses of these two component compounds should be the same. Further, even when two or more compounds chosen from the group consisting of compounds expressed by the formulas (Ia), (Ib) and (Ic) are mixed and the mixture is added to a nematic liquid crystal composition, the respective twist senses of these compounds should be the same.

The helical twist senses of these optically active compounds may be confirmed according to a known method such as contact method (see G. W. Gray and D. G. McDonnell, Mol. Cryst. Liq. Cryst., Vol. 34 (Letters), (1977), pp211).

The content of the optically active substances used as a component for the liquid crystal composition of the present invention, in the resulting liquid crystal composition, is in the range of 0.05 to 10 wt. %, preferably 0.05 to 5 wt. %, in terms of the content of a compound alone, in the case where a compound selected from the group consisting of compounds expressed by the formulas (Ia), (Ib) and (Ic) is singly added, or in terms of the content of the total of a compound selected from the group consisting of compounds expressed by the formulas (Ia), (Ib) and (Ic) and a compound expressed by the formula (II). If the quantity of optically active substances added is less than 0.05 wt. %, it is impossible to adjust the helical pitch of the resulting liquid crystal composition to desired length, while if it exceeds 10 wt. %, the nematic phase temperature range of the resulting liquid crystal composition is notably narrow.

Next, advantages brought about by the present invention will be described.

(i) Since the liquid crystal composition of the present invention has a notably increased twistability with temperature rise, it is possible to obtain a liquid crystal display element having a small temperature dependency of the threshold voltage by the use of the composition.

(ii) A liquid crystal composition of which the twistability is constant in a certain temperature range is easily prepared; hence by employing this composition for displays of SBE mode, DGH mode, phase change mode and other modes, it is easy to obtain a liquid crystal display element having a broad angle of view, a high contrast and a high response speed.

(iii) A liquid crystal composition having optionally controlled the change of the twistability ($P^{-1}$) depending on temperature is easily obtained; hence when it is applied to TN mode, a good liquid crystal display element having a slight reduction in the display quality depending on the ambient temperature change is obtained.

(iv) In the case of the liquid crystal composition of the present invention, optically active substances each having the same helical twist sense are used; hence there occurs no reversal of twist of the liquid crystal molecules which is inherent of the composition containing optically active substances of opposite twist senses to one another.

(v) Since optically active substances each having the same helical twist sense are used, a small quantity thereof added affords a desired pitch as compared with the case where an optically active substance having a right twist and that having a left twist are mixed and used.

(vi) Since a small quantity of the optically active substance is sufficient to afford a desired pitch, the properties of the original liquid crystal composition are not influenced so much by the addition thereof.

(vii) It is possible to produce a nematic composition relatively cheaply by adding a small quantity of the optically active substances which are generally expensive as compared with nematic compounds.

(viii) Since optically active substances each having the same twist sense are used, it is unnecessary to limit the mixing proportion as in the case where optically active substances each having a right twist and a left twist are mixed and used; hence it is easy to control the temperature dependency of the intrinsic helical pitch.

In addition to the above effectiveness (i)~(viii), the effectiveness of the present invention will be further described in the following Examples.

The present invention will be described in more detail by way of Examples, but it should not be construed to be limited thereto.

The helical pitch P described in Example was measured according to Cano wedge method.

EXAMPLE 1

To a nematic liquid crystal composition (D) (100 parts by weight) consisting of

 10 wt. %

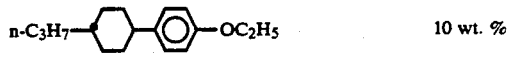 10 wt. %

 6 wt. %

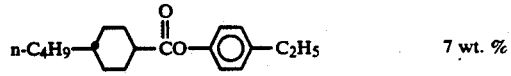 7 wt. %

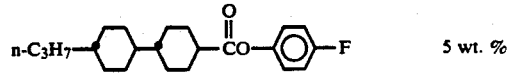 5 wt. %

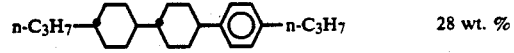 28 wt. %

-continued

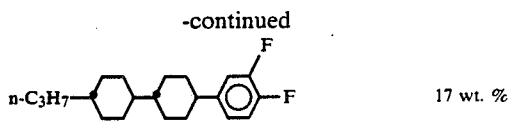 17 wt. % and

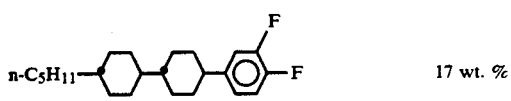 17 wt. % was added a compound B-3 (one part by weight) expressed by the formula

Figure 7:
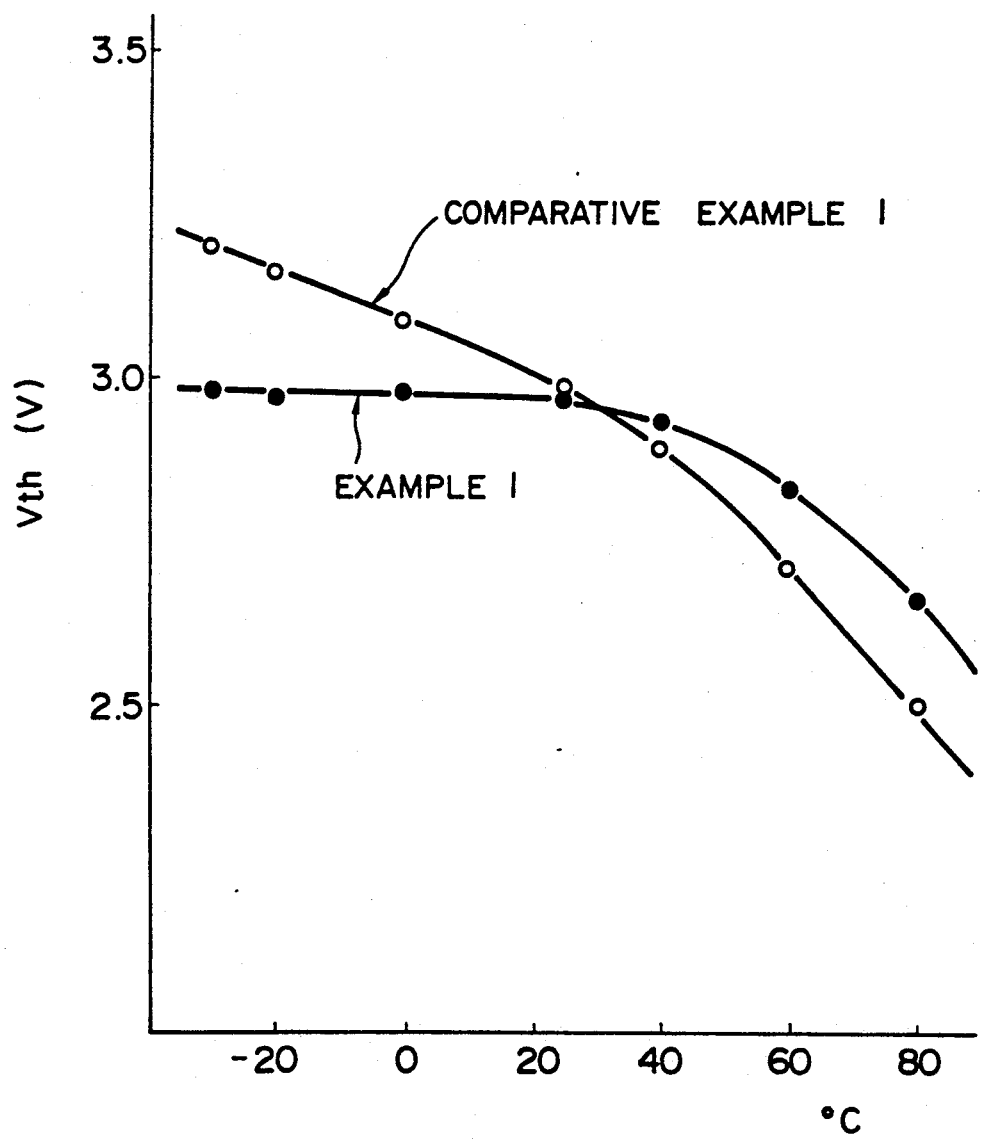

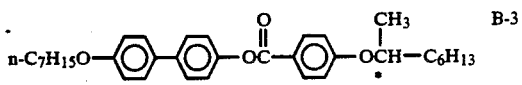

as an optically active substance, which compound is disclosed in Japanese patent application laid-open No. Sho 61-43 (1986); is obtained using R(−)-2-octanol as a starting raw material; and has a right helical twist sense, to prepare a nematic liquid crystal composition. This composition was sealed in a cell provided with substrates having the surface coated with polyvinyl alcohol and subjected to rubbing treatment and having a cell gap of 9 μm to prepare a TN liquid crystal cell. The threshold voltage of this TN liquid crystal cell was measured at various temperatures. The results are shown in FIG. 7.

When the temperature dependency of the threshold voltage is shown by the value of $\Delta V_{th}/\Delta t$ expressed by the following equation (5):

$$\frac{\Delta V_{th}}{\Delta t} = \frac{V_{th}(t_1) - V_{th}(t_2)}{t_1 - t_2} \times 1000 \quad (5)$$

wherein $V_{th}(t)$ represents a threshold voltage at a temperature of t° C., the temperature dependency of the TN liquid crystal cell is shown in Table 3. It is believed that the dependency is due to the fact that the temperature dependency $\Delta P^{-1}$ of the twistability of the nematic liquid crystal composition obtained by the addition of the compound B-3 has a positive value, as described later.

TABLE 3

|  | Ex. 1 | Comp. ex. 1 |
|---|---|---|
| $\Delta V_{th}/\Delta t$ | −30~25° C. | 0.0 | −3.8 |
|  | 25~80° C. | −5.5 | −8.7 |

COMPARATIVE EXAMPLE 1

To the nematic liquid crystal composition (D) (100 parts by weight) shown in Example 1 was added the above optically active substance C-1 (0.1 part by weight) to prepare a nematic liquid crystal composition, which was then sealed in the same cell as in Example 1 to measure the threshold voltage. The results are shown in FIG. 7 together with those of Example 1. Further the temperature dependency of the threshold voltage is shown in Table 3.

EXAMPLE 2 AND COMPARATIVE EXAMPLE 2

To the nematic liquid crystal composition (D) (100 parts by weight) was added a compound B-4 (1.6 part by weight) expressed by the formula

Figure 8:
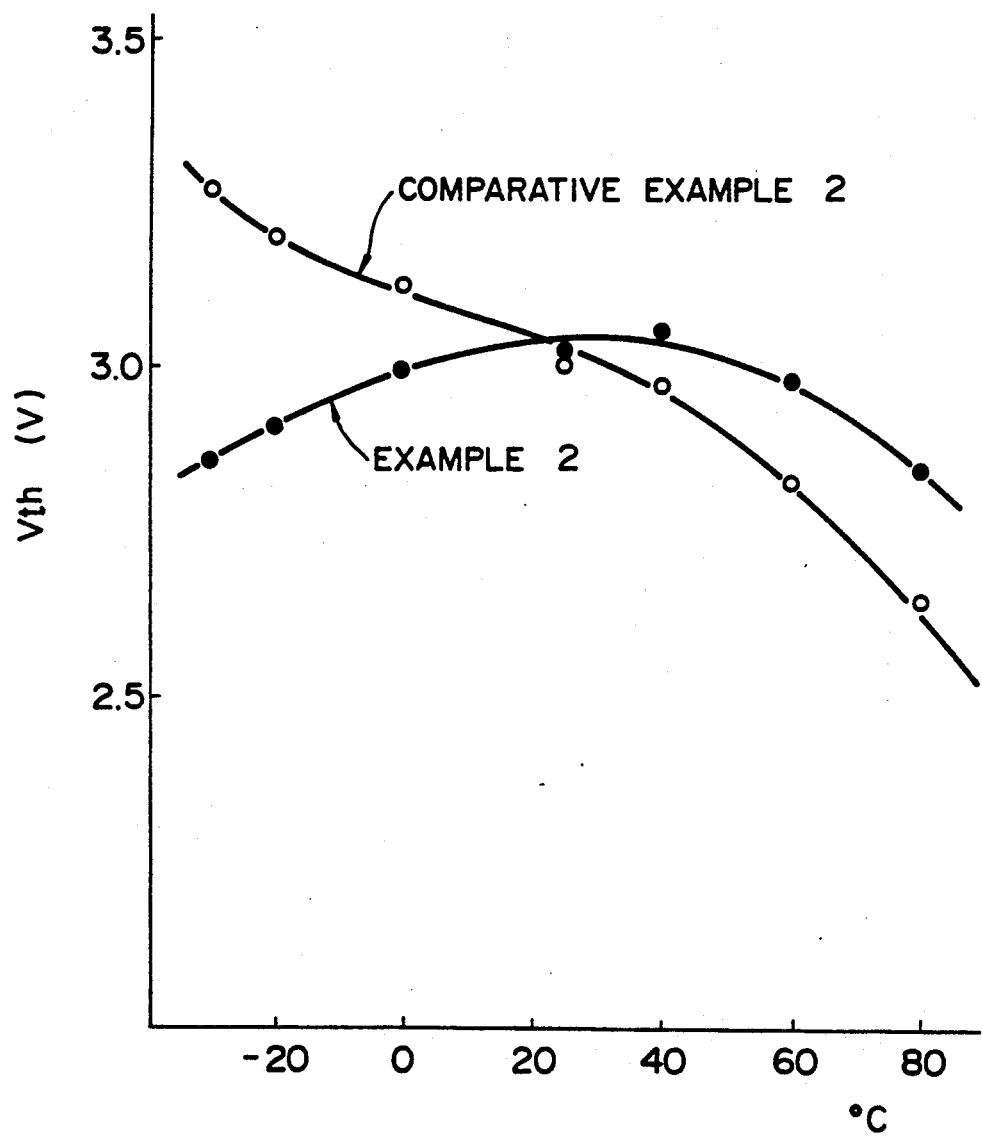

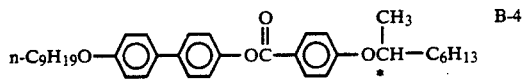

as an optically active substance, which compound is also disclosed in the above Japanese patent application laid-open No. Sho 61-43; is obtained using S(+)-2-octanol as a starting raw material; and has a left helical twist sense, to prepare a nematic liquid crystal composition, which was then sealed in the same TN cell as in Example 1 to measure the threshold voltage. The results are shown in FIG. 8. Further, from the results of FIG. 8 was calculated the temperature dependency of the threshold voltage $\Delta V_{th}/\Delta t$. The results are shown in Table 4.

As a comparative example, to the liquid crystal composition (D) (100 parts by weight) was added cholesteryl nonanoate (0.2 part by weight) to prepare a nematic liquid crystal composition, from which was prepared the same TN liquid crystal cell as in Example 2, followed by measuring its temperature dependency of the threshold voltage. The results are shown in FIG. 8 and Table 4 together with those of Example 2.

TABLE 4

|  |  | Ex. 2 | Comp. ex. 2 |
|---|---|---|---|
| $\Delta V_{th}/\Delta t$ | −30~25° C. | +3.3 | −4.7 |
|  | 25~80° C. | −3.3 | −6.5 |

In comparison of Example 2 with Comparative example 2, the temperature dependency of the threshold voltage $\Delta V_{th}/\Delta t$ between 25° and 80° C. of Example 2 is about half of that of Comparative example 2. Further, on the lower temperature side, the value of $\Delta V_{th}/\Delta t$ of Example 2 is a positive value contrarily to conventional temperature dependency of the threshold voltage.

As apparent from FIG. 8, there is the maximum value of the threshold voltage $V_{th}$ in the vicinity of 30° C. in the case of Example 2. This is considered to be due to the fact that on the lower temperature side, increase in the intrinsic helical pitch has a greater influence upon the temperature change of $V_{th}$ than the effects brought about by the temperature change in the elastic constant and other properties of the composition, whereas on the higher temperature side, the effect brought about by the temperature change in the elastic constant is notable. The fact that a maximum value appears in the threshold voltage as described above is a phenomenon which has never been observed in the so far known liquid crystal compositions.

In the case of the prior art, as the temperature lowers, the threshold voltage $V_{th}$ of the liquid crystal display element increases monotonously, and approaches a definite driving voltage up to a certain value; thus along with the influence of increase in the viscosity of the liquid crystal, the response speed of the display lowers.

Whereas, by using the composition of the present invention, it is possible to inhibit the $V_{th}$ reduction on the higher temperature side, and also it is possible to inhibit the $V_{th}$ rise on the lower temperature side; hence the difference between the definite driving voltage and the threshold voltage may be kept to a certain value over the practical temperature range so that it is possible to compensate the lowering of the response speed due to the viscosity rise in the lower temperature region. Further, since it is possible to reduce the temperature dependency of the threshold voltage, that is, it is possible to reduce the absolute value of $|\Delta V_{th}/\Delta t|$, a superior display in the aspect of the contrast is obtained over a broad temperature range.

EXAMPLE 3

To the nematic liquid crystal composition (D) (100 parts by weight) shown in Example 1 was added a compound B-5 (0.25 part by weight) expressed by the formula

Figure 9:
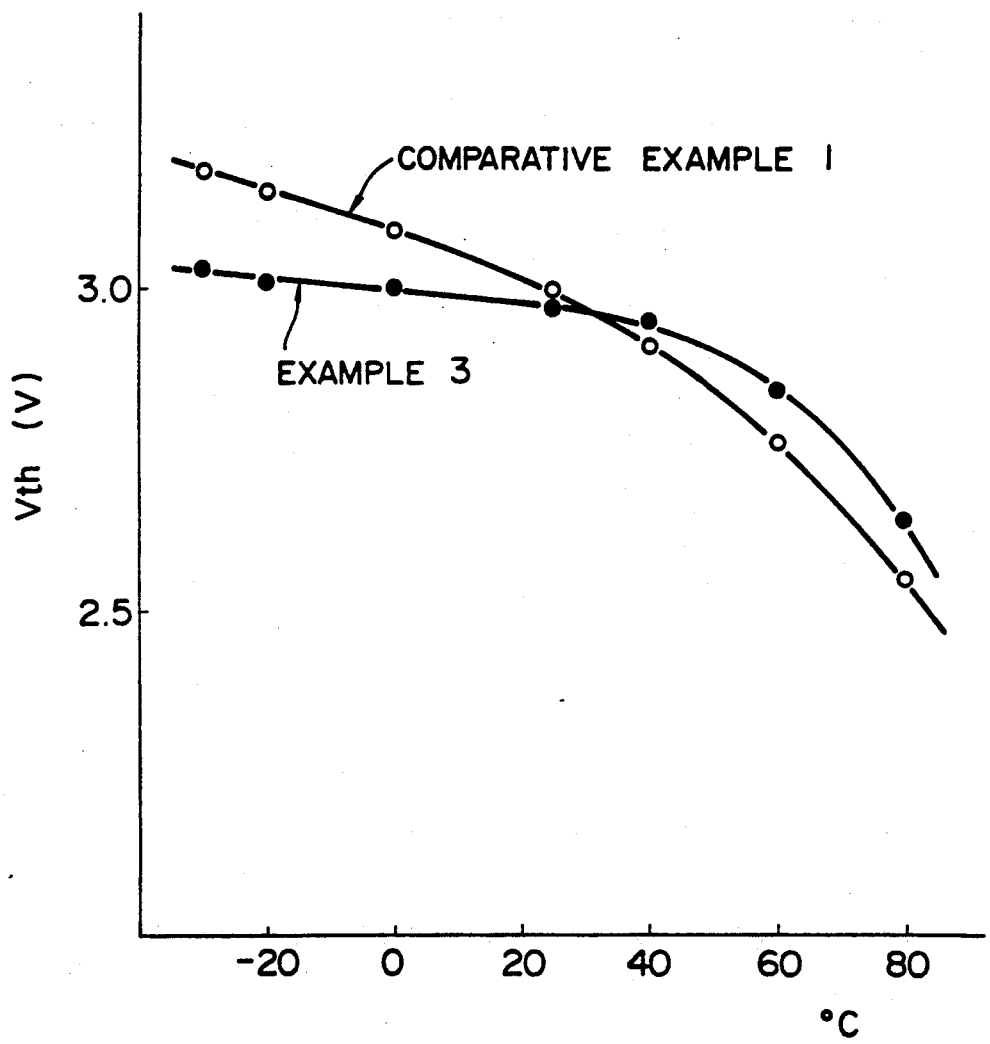

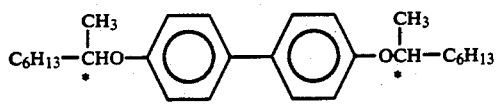

as an optically active substance, which compound is obtained using R(−)-2-octanol as a starting raw material and has a right helical twist sense, to prepare a nematic liquid crystal composition, which was then sealed in the same TN cell as in Example 1 to measure its threshold voltage. The results are shown in FIG. 9. Further, from the results in FIG. 9 was calculated the temperature dependency of the threshold voltage ($\Delta V_{th}/\Delta t$). The results are shown in Table 5.

For comparison, the results of Comparative example 1 are again shown in FIG. 9 and Table 5.

TABLE 5

|  |  | Example 3 | Comparative example 1 |
|---|---|---|---|
| $\Delta V_{th}/\Delta t$ | −30~25° C. | −1.1 | −3.8 |
|  | 25~80° C. | −6.0 | −8.7 |

In Example 3, it is seen that the temperature dependency of the threshold voltage was considerably reduced.

EXAMPLE 4

Figure 10:
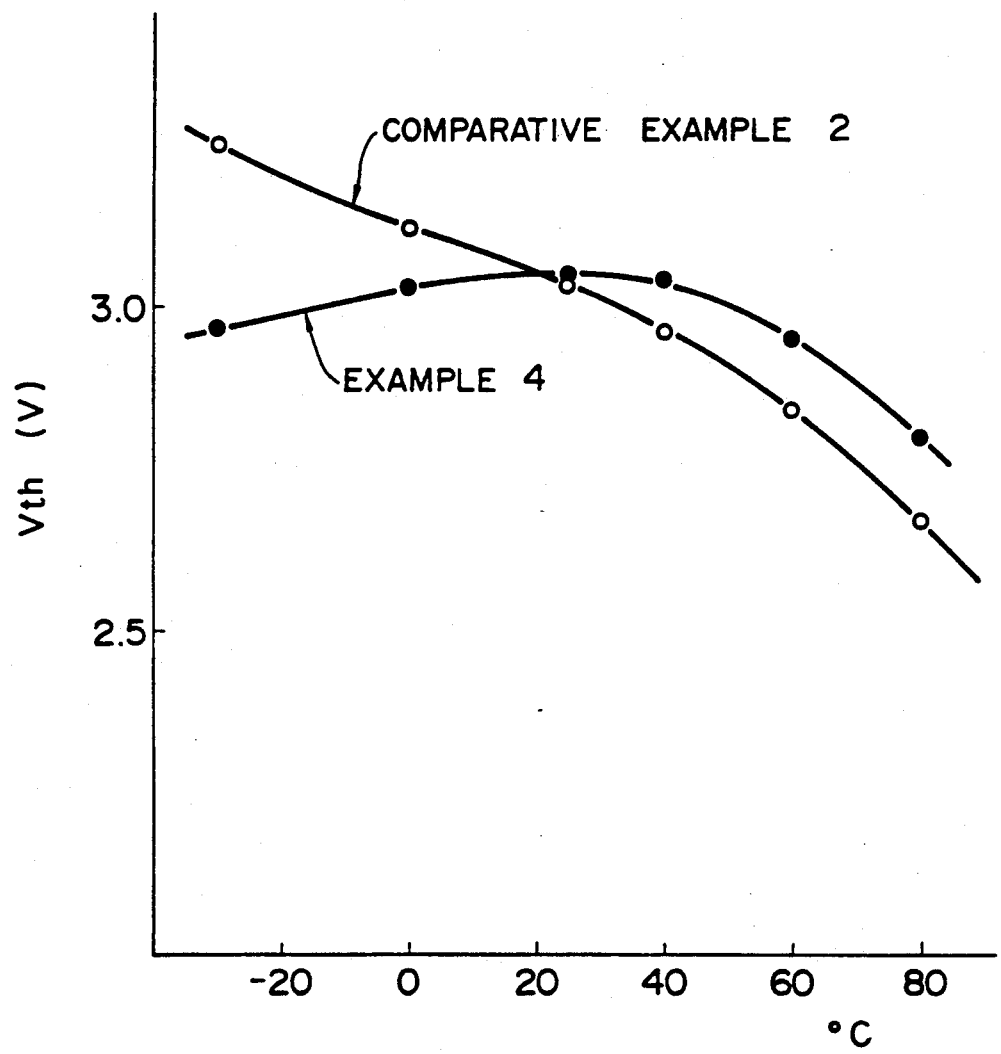

To the nematic liquid crystal composition (D) (100 parts by weight) shown in Example 1 was added a compound B-6 (0.5 part by weight) as an optically active substance, which compound is expressed by the same formula as that of the compound B-5 shown in Example 3 but is obtained using S(+)-2-octanol as a starting raw material and has a left helical twist sense, to prepare a nematic liquid crystal composition, which was then sealed in the same cell as in Example 1 to measure its threshold voltage. The results are shown in FIG. 10. Further, from the results in FIG. 10 was calculated the temperature dependency of the threshold voltage ($\Delta V_{th}/\Delta t$). The results are shown in Table 6. For comparison, the results of Comparative example 2 are again shown in FIG. 10 and Table 6.

TABLE 6

|  |  | Example 4 | Comparative example 2 |
|---|---|---|---|
| $\Delta V_{th}/\Delta t$ | −30~25° C. | +1.5 | −4.7 |
|  | 25~80° C. | −4.5 | −6.5 |

In the case of Example 4, there is shown a tendency that the temperature dependency of the threshold voltage in the lower temperature region is contrary to conventional one, as in the case of Example 2.

EXAMPLE 5 AND COMPARATIVE EXAMPLE 3

The following ten compounds of B-7 to B-16 as optically active substances belonging to the compounds respectively expressed by the formula (Ia), (Ib) or (Ic), and the above-mentioned six compounds of B-1 to B-6, were respectively singly and in a quantity of 1 to 5 parts by weight added to the above nematic liquid crystal composition (A) (100 parts by weight) referred to in the afore-mentioned description of the prior art, to prepare sixteen nematic liquid crystal compositions:

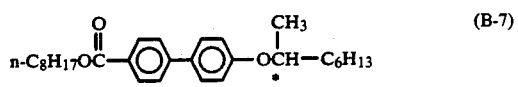
(B-7)

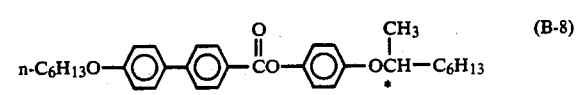
(B-8)

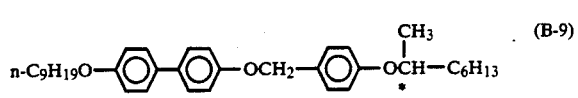
(B-9)

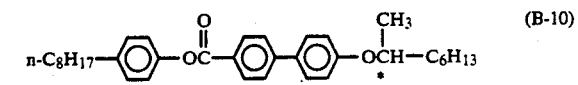
(B-10)

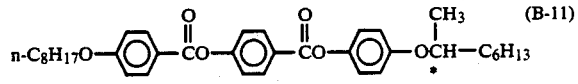
(B-11)

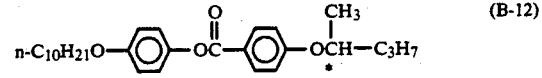
(B-12)

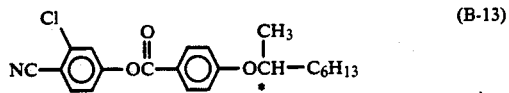
(B-13)

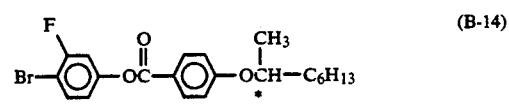
(B-14)

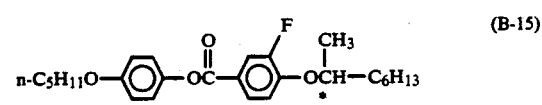
(B-15)

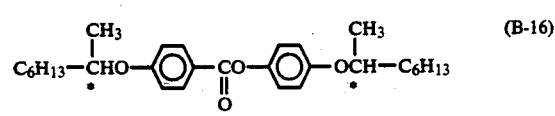
(B-16)

As to these nematic liquid crystal compositions, their intrinsic helical pitches were measured at various temperatures according to Cano wedge method, and the temperature dependency of the twistability calculated from the results is shown in terms of normalized values of $\Delta P^{-1}_{20\sim40}$ in Table 7. For comparison, to the nematic liquid crystal composition (A) (100 parts by weight) were added the following six optically active substances C-5 to C-10 belonging to the group of the compounds expressed by the formula (II) and the above four optically active compounds C-1 to C-4, respectively singly and in a quantity of 0.5 to 5 parts by weight, to prepare ten nematic liquid crystal compositions, followed by measuring their intrinsic helical pitches in the same manner as in Example 5, to calculate their temperature dependencies of the twistability. The resulting values of $\Delta P^{-1}{}_{20\sim40}$ are shown in Table 7.

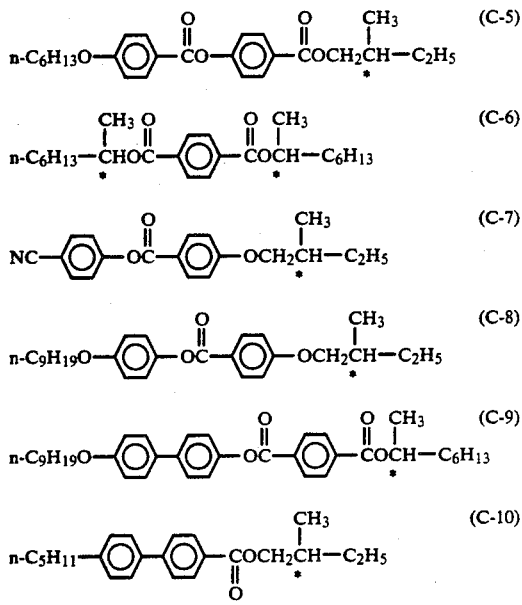

TABLE 7

| Example 5 | | Comparative example 3 | |
|---|---|---|---|
| Compound added | $\Delta P^{-1}\,20\sim40$ | Compound added | $\Delta P^{-1}\,20\sim40$ |
| B-1 | 1.93 | C-1 | −0.48 |
| -2 | 0.92 | -2 | −0.26 |
| -3 | 1.88 | -3 | −0.28 |
| -4 | 1.93 | -4 | −0.75 |
| -5 | 0.77 | -5 | −0.63 |
| -6 | 0.77 | -6 | −0.94 |
| -7 | 1.31 | -7 | −0.68 |
| -8 | 1.35 | -8 | −0.43 |
| -9 | 1.86 | -9 | −0.13 |
| -10 | 1.09 | -10 | −0.69 |
| -11 | 1.05 | | |
| -12 | 0.57 | | |
| -13 | 1.61 | | |
| -14 | 1.85 | | |
| -15 | 0.38 | | |
| -16 | 0.84 | | |

As described above, the composition in the first aspect of the present invention is characterized in that the value of $\Delta P^{-1}$ representing the temperature dependency of the twistability is a positive value, and as its effectiveness, it is possible to inhibit reduction in the threshold voltage of liquid crystal display elements using the composition of the present invention, accompanying the temperature rise.

EXAMPLE 6

Figure 11:
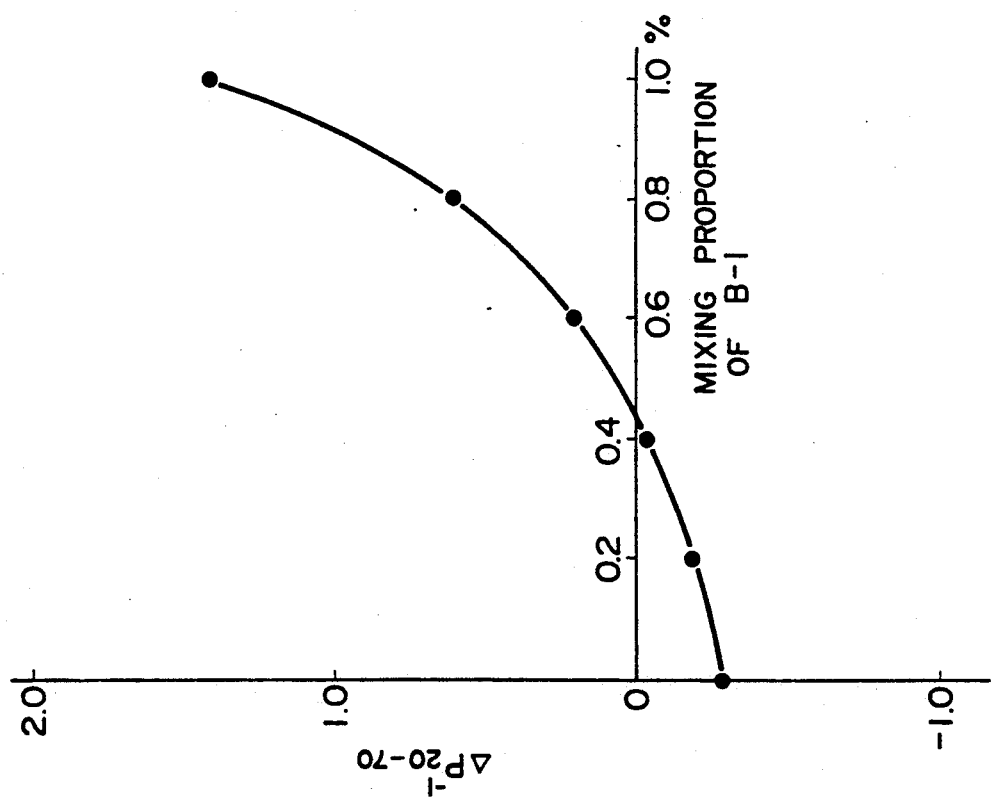

To the above nematic liquid crystal composition (A) were added the above optically active substances B-1 and C-3, in various mixing proportions but so as to give a total quantity of 1% by weight, to measure the temperature dependency of the twistability ($P^{-1}$) of the resulting liquid crystal composition. The fact that the optically active compounds B-1 and C-3 had the same twist sense was confirmed according to contact method. Change in the $\Delta P^{-1}{}_{20\text{-}70}$ in varied mixing proportions of B-1 and C-3 is shown in FIG. 11. When the quantity of B-1 added is 0.43% by weight, $\Delta P^{-1}=0$. This indicates that the intrinsic pitch P is unchanged between 20° C. and 70° C. at this mixing proportion.

COMPARATIVE EXAMPLE 4

Figure 12:
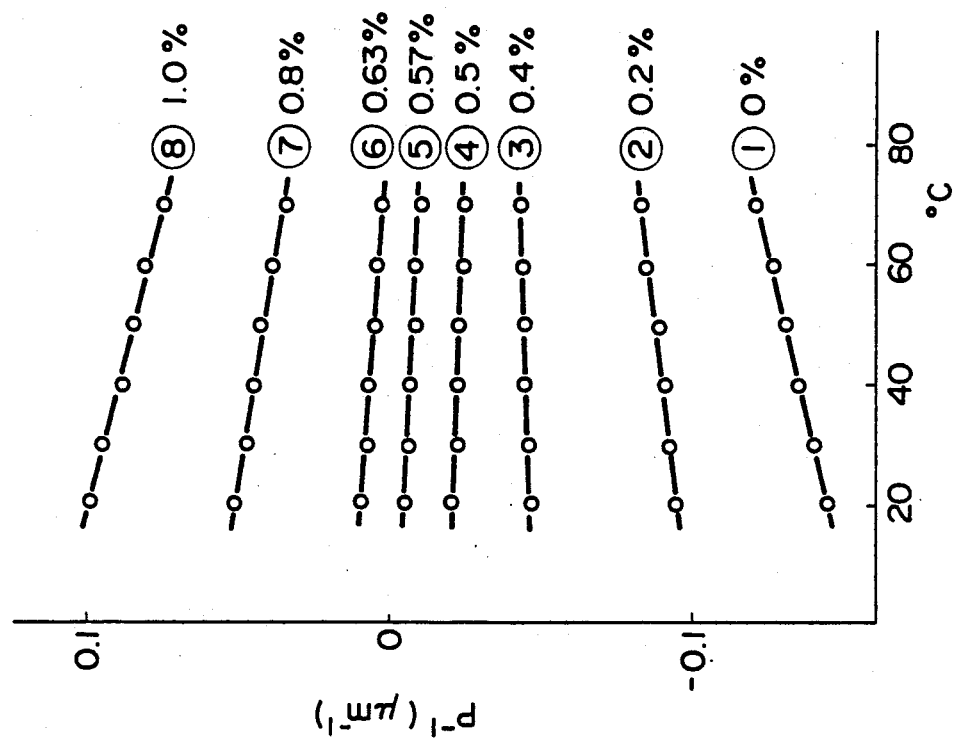

The above optically active substance C-1 and the above optically active substance C-2 having an opposite twist sense to that of the above substance C-1 were added in varied mixing proportions but so as to give a total quantity of 1% by weight, to the above nematic liquid crystal composition (A) to measure the temperature dependencies of the twistability $P^{-1}$ of the resulting liquid crystal compositions. Results in the case where the quantity of C-1 added was varied from 0% by weight to 1% by weight at intervals of about 0.2% by weight are shown in FIG. 12.

There is expected a temperature at which $P^{-1}=0$ in the vicinity of the quantity of C-1 added of 0.6% by weight, and $P^{-1}$ takes a negative or positive value below or above this temperature.

Figure 13:
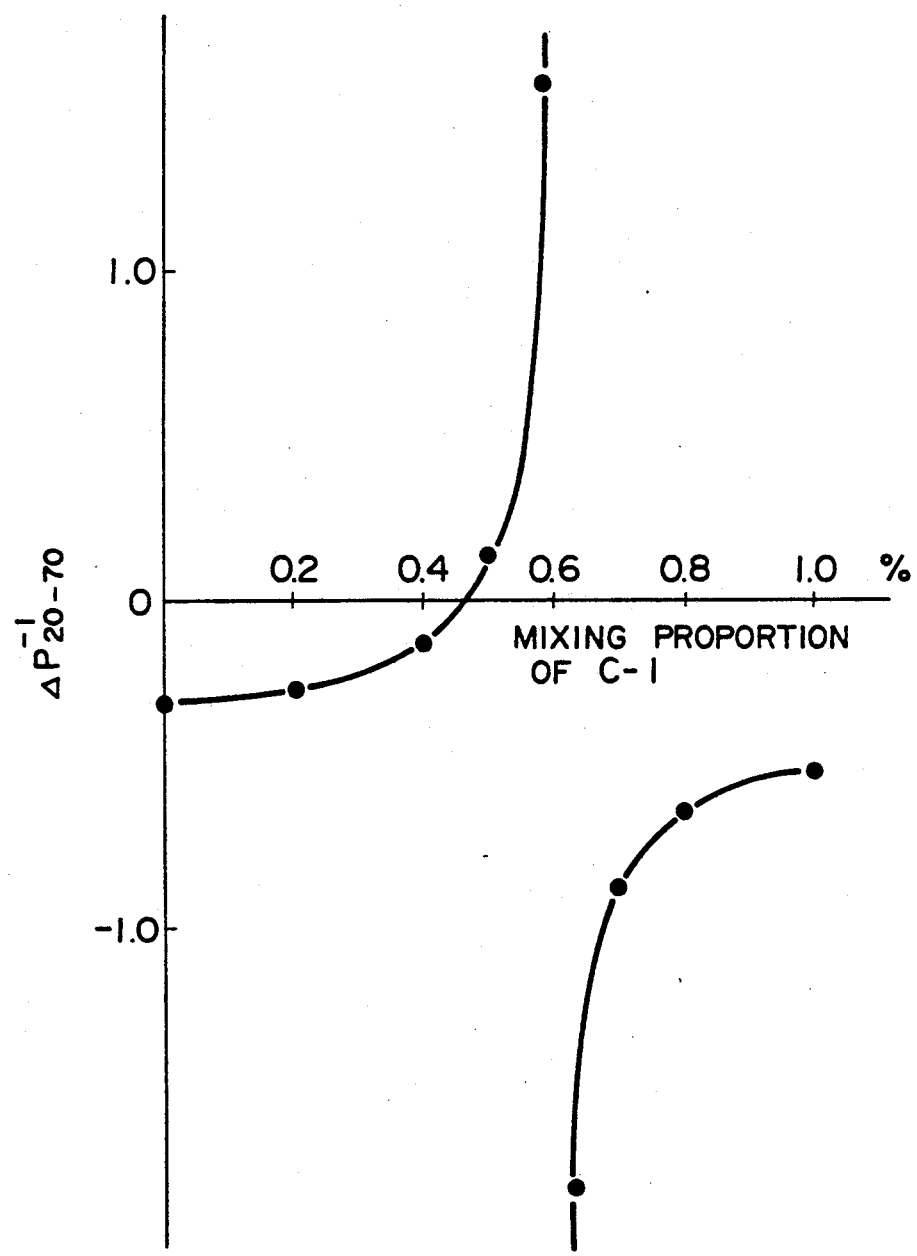

The change of $\Delta P^{-1}$ between 20° C. and 70° C. in varied mixing proportions of C-1 and C-2 is shown in FIG. 13.

When the quantity of C-1 added is 0.46% by weight, $\Delta P^{-1}=0$, but when it is in the vicinity of 0.6% by weight, there is a temperature at which $P^{-1}=0$ and $\Delta P^{-1}$ is divergent. This is because, as apparent from the equation (4), since the sign of $P^{-1}(20)$ and $P^{-1}(70)$ are different, the absolute value of the ratio of the difference between $P^{-1}(20)$ and $P^{-1}(70)$ to the sum of the two is necessarily 1 or more and $|\Delta P^{-1}{}_{20\text{-}70}|$ is necessarily 4 or more. Equation of $P^{-1}(20)=-P^{-1}(70)$ comes into existence in a certain mixing ratio in which the denominator of the right side term of the equation (4) approaches zero; hence $\Delta P^{-1}$ is divergent.

In comparison of Example 6 with Comparative example 4, $\Delta P^{-1}$ slowly changes in the case of Example 6; whereas in the case of Comparative example 4, since two kinds of optically active substances having right twist and left twist, respectively are mixed, there is a mixing proportion in which $\Delta P^{-1}$ is divergent. Further, in comparison of the ranges of mixing proportion within which $P^{-1}$ is almost unchanged (i.e. $-0.1 \leq \Delta P^{-1} \leq 0.1$), the range in the case of Example 6 is as relatively broad as 0.32~0.53% by weight, whereas the range in the case of Comparative example 4 is 0.41~0.49% by weight, that is, only half of the range in the case of Example 6. Since the range of mixing proportion within which $\Delta P^{-1} \approx 0$, in the case of Example 6 is broader than that in the case of Comparative example 4, it is seen that the intrinsic pitch is easily made constant irrespective of temperature.

In comparison of the ranges of mixing proportion within which $P^{-1}$ increases with temperature rise ($\Delta P^{-1} \geq 0.1$), the range in the case of Example 6 is as very broad as 0.53~1.0% by weight, whereas the range in the case of Comparative example 4 is as very narrow as 0.5~0.59% by weight, i.e. just before $\Delta P^{-1}$ is divergent. Since the range of mixing proportion with which $\Delta P^{-1} \geq 0.1$, in the case of Example 6, is much broader than that in the case of Comparative example 4, the temperature dependency of the intrinsic pitch is more easily controlled in the case of Example 6. Further, $P^{-1}$ at 20° C. in the case of $\Delta P^{-1}=0$ was roughly estimated employing the above equation (3). The results are shown in Table 8.

TABLE 8

|  | Example 6 | Comparative example 4 |
|---|---|---|
| $P^{-1}$ (20) | 0.036 | 0.028 |

The value of $P^{-1}$(20) in Example 6 is larger than that in Comparative example 4. Further, comparison of $P^{-1}$s at 20° C. in the case where $\Delta P^{-1}$ is larger, is shown in Table 9.

TABLE 9

|  | Example 6 | Comparative example 4 |
|---|---|---|
| $\Delta P^{-1}$ 20-70 | 1.41 | 1.58 |
| $P^{-1}$ (20) | 0.0104 | 0.0044 |

In this Table, close values of $\Delta P^{-1}{}_{20-70}$ are chosen. The value of $P^{-1}{}_{(20)}$ in the case of Comparative example 4 is less than half of that in the case of Example 6. This indicates that in order to obtain a definite intrinsic pitch, as apparent from the equation (1), the quantity of optically active substances added in the case of Example 6 may be sufficient to be less than half of that in the case of Comparative example 4. This fact that a small quantity of optically active substances added may be sufficient affords two advantages that the resulting composition is cheap as much and the influence which the addition has upon the characteristics of the original nematic liquid crystal composition is small.

EXAMPLE 7

Figure 14:
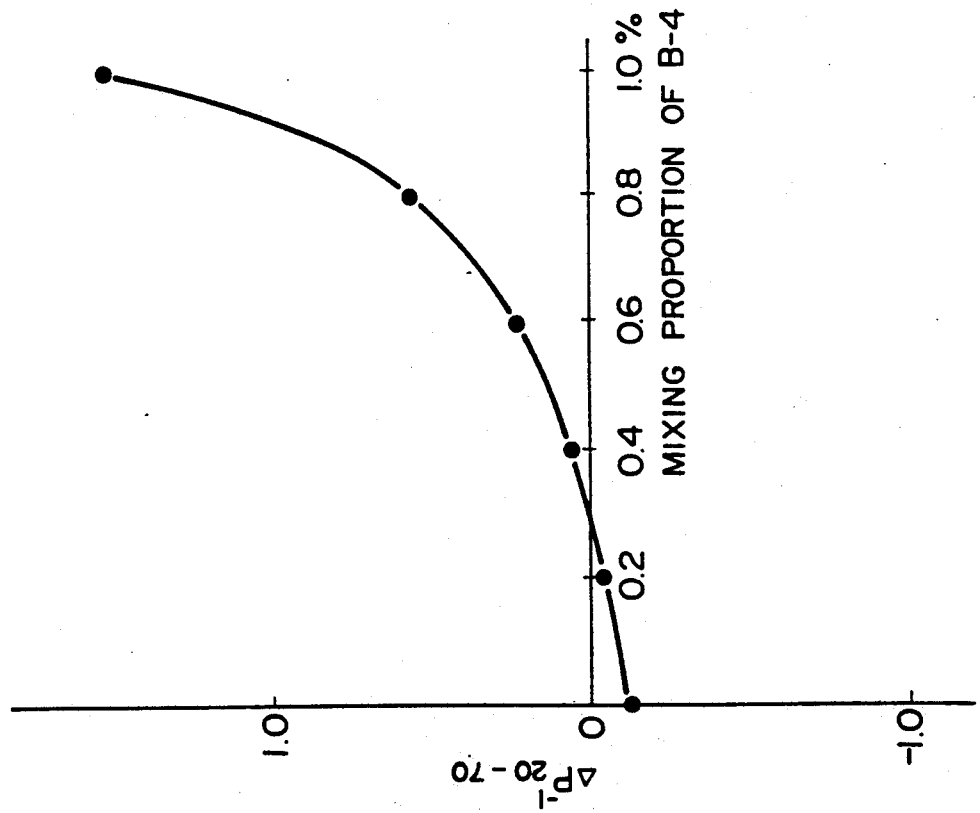

The above optically active substance B-4 included in the group of compounds expressed by the formula (III) and obtained using S(+)-2-octanol as a starting raw material and having a left twist sense, and the above optically active substance C-9 included in the formula (VII), and obtained using S(+)-2-octanol as a starting raw material and having the same i.e. left twist sense, were added in varied mixing proportions but so as to give a total quantity of 1% by weight, to the above nematic liquid crystal composition A, to measure the temperature dependency of the twistability $P^{-1}$ of the resulting liquid crystal composition. The fact that the twist senses of the optically active substances B-4 and C-9 are the same was confirmed according to contact method. Change of $\Delta P^{-1}{}_{20-70}$ in varied mixing proportions of B-4 and C-9 is shown in FIG. 14. When the quantity of B-4 added is 0.28% by weight, $\Delta P^-=0$. The mixing proportion of B-4 in which $\Delta P^{-1} \approx 0$ ($-0.1 \leq \Delta P^{-1} \leq 0.1$) is as very broad as 0.04~0.46% by weight. Further, the mixing proportion of B-4 in which $\Delta P^{-1} \geq 0.1$ is as very broad as 0.46~1.0% by weight.

COMPARATIVE EXAMPLE 5

Figure 15:
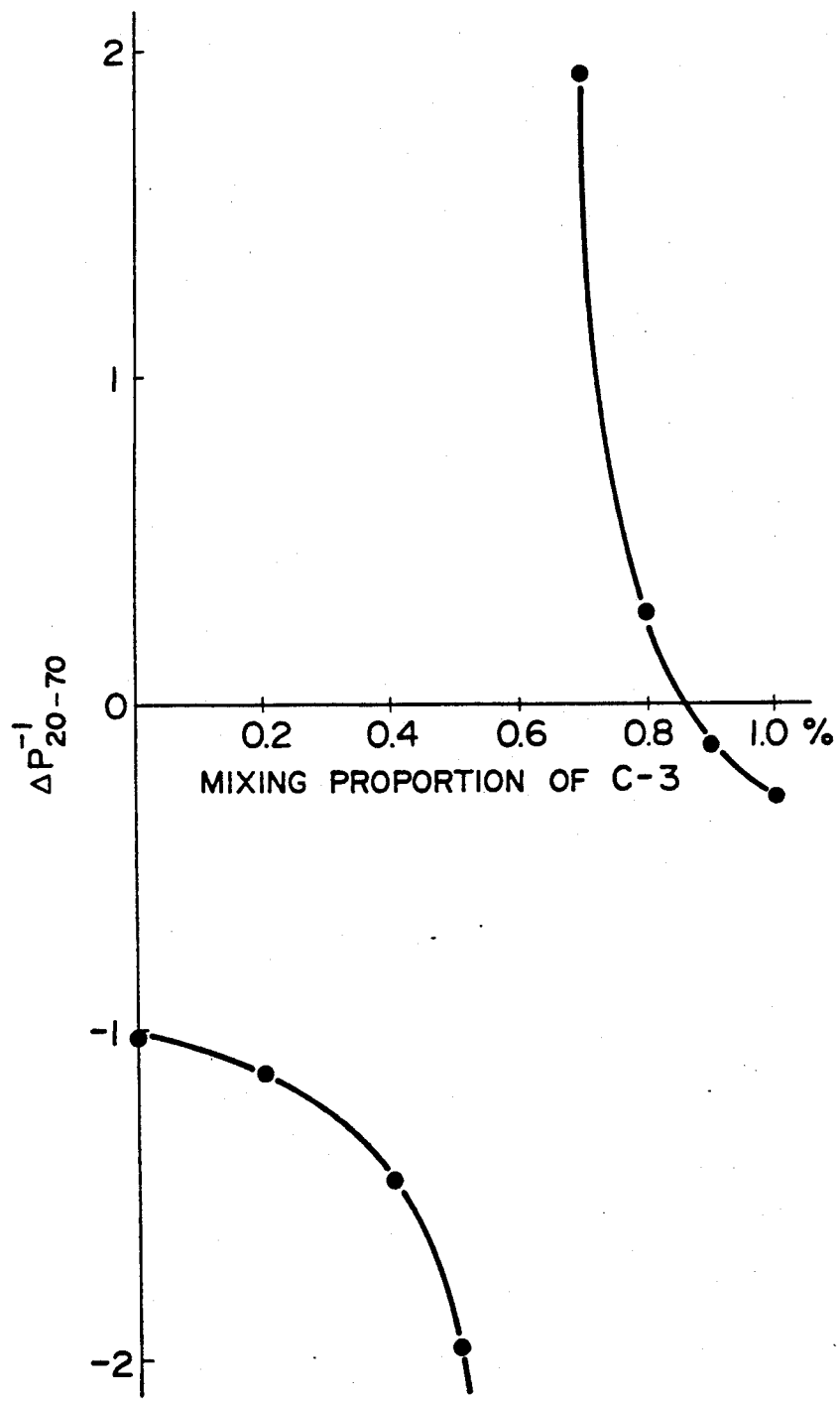

The above optically active substance C-3 and the above optically active substance C-6 having an opposite twist sense to that of the former substance were added to the above nematic liquid crystal composition (A) in varied mixing proportions but so as to give a total quantity of 1% by weight, to measure the temperature dependency of the twistability $P^{-1}$ of the resulting liquid crystal composition. The change of $\Delta P^{-1}{}_{20-70}$ in varied mixing proportions of C-3 and C-6 is shown in FIG. 15. When the quantity of C-3 added is 0.86% by weight, $\Delta P^{-1}=0$. The range of the quantity thereof added in which $\Delta P^{-1} \approx 0$ ($-0.1 \leq \Delta P^{-1} \leq 0.1$) is as narrow as 0.83~0.89% by weight. Further, $\Delta P^{-1}$ is also divergent. Further the mixing proportion in which $\Delta P^{-1} \geq 0.1$ has as narrow a range as 0.83~0.7% by weight and is in the vicinity where $\Delta P^{-1}$ is divergent.

The range of the mixing proportion in which $\Delta P^{-1} \approx 0$ in the case of Example 7 is much broader than that in the case of Comparative example 5; hence the intrinsic pitch P is easily made constant irrespective of temperature. Further, the range of the mixing proportion in which $\Delta P^{-1} \geq 0.1$ in the case of Example 7 is much broader than that in the case of Comparative example 5; hence it is easy to control the temperature dependency of the intrinsic pitch P in order to reduce the temperature dependency of the threshold voltage $V_{th}$. Further, $P^{-1}$ at 20° C. in the case of $\Delta P^{-1}=0$ was roughly estimated. The results are shown in Table 10.

TABLE 10

|  | Example 7 | Comparative example 5 |
|---|---|---|
| $P^{-1}$ (20) | 0.061 | 0.032 |

The value of $P^{-1}{}_{(20)}$ in the case of Comparative example 5 is about a half of that in the case of Example 7. Further, comparison of $P^{-1}$s at 20° C. in the case of larger $\Delta P^{-1}$ is shown in Table 11.

TABLE 11

|  | Example 7 | Comparative example 5 |
|---|---|---|
| $\Delta P^{-1}$ 20-70 | 1.52 | 1.92 |
| $P^{-1}$ (20) | 0.0101 | 0.0056 |

The $P^{-1}{}_{(20)}$ value in the case of Comparative example 5 is about a half of that in the case of Example 7. In short, the quantity of optically active substances added, in the case of Example 7, may be sufficient to be a half of that in the case of Comparative example 5; hence Example 7 is superior in that the resulting composition is cheaper and the effect upon the characteristics of the original nematic liquid crystal composition is small.

EXAMPLE 8

The above optically active substance B-4 belonging to the group of compounds expressed by the formula (IV); described in Japanese patent application No. Sho 60-283110/1985 (filed by Chisso Corporation); obtained using R(−)-2-octanol as a starting raw material; and having a right helical twist sense, and the above optically active substance C-3 having the same twist sense as that of the above substance, were added in varied mixing proportions but so as to give a total quantity of 1% by weight, to the above nematic liquid crystal composition (A), to measure the temperature dependency of the twistability $P^{-1}$ of the resulting liquid crystal composition. The fact that B-14 and C-3 have the same twist sense was confirmed according to contact method.

Figure 16:
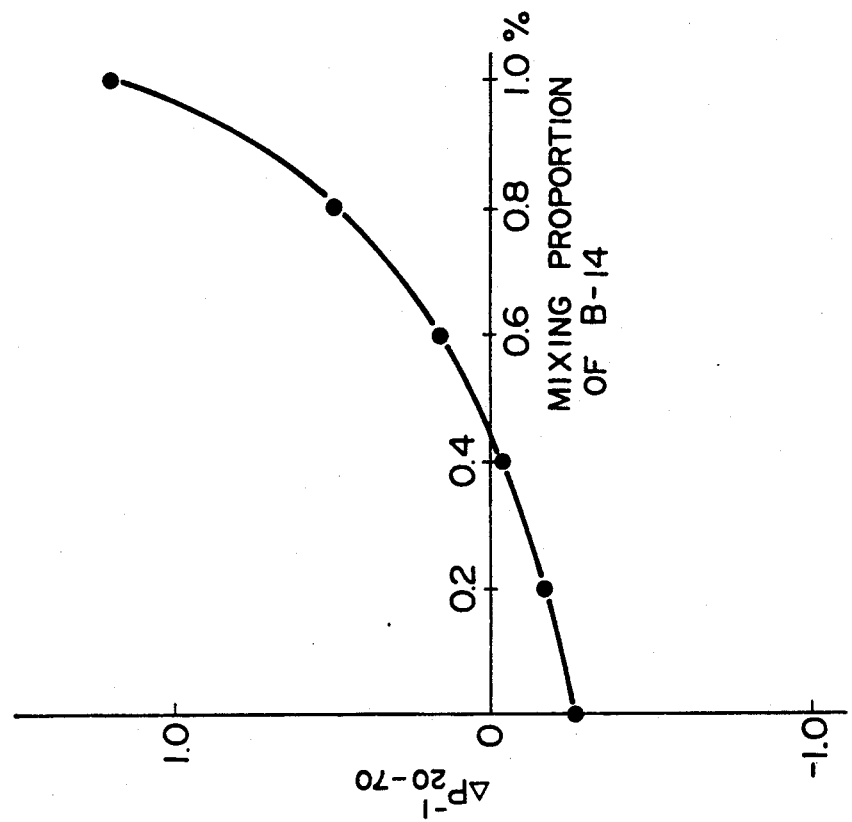

The change of $\Delta P^{-1}{}_{20-70}$ in varied mixing proportions of B-14 and C-3 is shown in FIG. 16. When the quantity of B-14 added is 0.45% by weight, $\Delta P^{-1}=0$, and the mixing proportion of B-14 in which $\Delta P^{-1} \approx 0$ (i.e. $-0.1 \leq \Delta P^{-1} \leq 0.1$) has as very broad a range as 0.31–0.55% by weight. The mixing proportion in which $\Delta P^{-1} \geq 0.1$ has as broad a range as 0.55–1.0% by weight.

In comparison of Example 8 with Comparative example 5, the range of the mixing proportion in which $\Delta P^{-1} \approx 0$ in the case of Example 8 is much broader than that in the case of Comparative example 5; hence the intrinsic pitch P is easily made constant irrespective of temperature. Further, the range of the mixing proportion in which $\Delta P^{-1} \geq 0.1$, in the case of Example 8, is much broader than that in the case of Comparative example 5; hence it is easy to control the temperature dependency of the intrinsic pitch P in order to reduce the temperature dependency of the threshold voltage $V_{th}$.

Further, $P^{-1}$ at 20° C. in the case of $\Delta P^{-1}=0$ was roughly estimated. The results are shown in Table 12.

TABLE 12

|  | Example 8 | Comparative example 5 |
|---|---|---|
| $P^{-1}$ (20) | 0.037 | 0.032 |

The value of $P^{-1}{}_{(20)}$ in the case of Example 8 is larger than that in the case of Comparative example 5.

Further, comparison of $P^{-1}$s at 20° C. in which $\Delta P^{-1}$ is large is shown in Table 13.

TABLE 13

|  | Example 8 | Comparative example 5 |
|---|---|---|
| $\Delta P^{-1}$ 20–70 | 1.21 | 1.92 |
| $P^{-1}$ (20) | 0.0094 | 0.0056 |

The value of $P^{-1}{}_{(20)}$ in the case of Example 8 is about twice the value in the case of Comparative example 5. In short, the quantity of optically active substance added in the case of Example 8 may be sufficient to be less than that in the case of Comparative example 5; hence Example 8 is superior in that the resulting composition is cheaper and also the effect upon the characteristics of the original nematic liquid crystal composition is small.

Examples 6, 7 and 8 indicate that when an optically active substance having a positive and very large $\Delta P^{-1}{}_{20-70}$, as expressed by the formula (III) or (IV), and an optically active substance having the same twist sense as that of the former substance and having a negative and relatively small $\Delta P^{-1}{}_{20-70}$ are combined, then it is possible to easily control the temperature dependency of the intrinsic pitch P in order to be free from the temperature dependency of the twistability $P^{-1}$ or to reduce the temperature dependency of the threshold voltage $V_{th}$. It is seen from these facts that in order to control the temperature dependency of the intrinsic pitch P to thereby reduce the temperature dependency of the threshold voltage $V_{th}$, the mixture of an optically active substance having a positive and large $\Delta P^{-1}$ value and an optically active substance having the same twist sense as that of the above substance and a negative value of $\Delta P^{-1}$ broadens range of mixing proportion in which $\Delta P^{-1} \geq 0$. Further, when the pitch of either components is shorter at room temperature, a smaller addition quantity thereof may be sufficient.

EXAMPLES 9~11 AND COMPARATIVE EXAMPLE 6

An optically active substance B-17 belonging to a group of compounds of the formula (III) and expressed by the formula

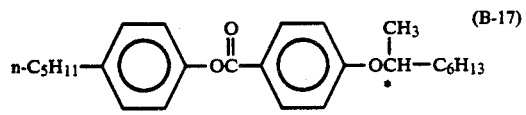

(B-17)

which substance is disclosed in Japanese patent application laid-open No. Sho 61-43; obtained using S(+)-2-octanol as a starting raw material; and has a left helical twist sense, and an optically active substance C-11 expressed by the formula

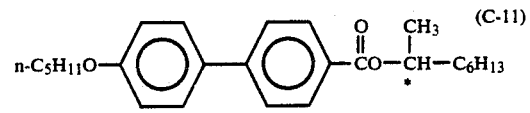

(C-11)

which substance has the same twist sense as that of the above substance; is disclosed in Japanese patent application laid-open No. Sho 60-149548; and is obtained using S(+)-2-octanol as a starting raw material, were added to the above nematic liquid crystal composition D in varied mixing proportions so as to give an intrinsic pitch at 25° C. of 80 μm, to prepare 4 kinds of nematic liquid crystal compositions shown in Table 14.

Table 14 shows the mixing proportions of B-17 and C-11 in the respective compositions, the total quantities of the two compounds added and the $\Delta P^{-1}{}_{20-40}$. The fact that the twist senses of the optically active substances B-17 and C-11 are the same was confirmed according to contact method.

TABLE 14

|  | Mixing proportion of B-17 | Total quantity added | $\Delta P^{-1}$ 20–40 |
|---|---|---|---|
| Example 9 | 2.4 wt. % | 2.4 wt. % | 1.79 |
| Example 10 | 0.75 wt. % | 0.83 wt. % | 1.21 |
| Example 11 | 0.40 wt. % | 0.50 wt. % | 0.55 |
| Comparative example 6 | 0 wt. % | 0.12 wt. % | −0.03 |

These 4 kinds of the compositions were sealed in the same TN cell as in Example 1 to measure their threshold voltages. The results are shown in FIG. 17, and from the results were calculated their temperature dependencies of the threshold voltages, which are shown in Table 15.

TABLE 15

|  | $\Delta V_{th}/\Delta t$ | |
|---|---|---|
|  | −30~25° C. | 25~80° C. |
| Example 9 | +10.7 | −3.5 |
| Example 10 | 0 | −6.7 |
| Example 11 | −1.8 | −7.3 |
| Comparative example 6 | −4.2 | −7.8 |

Figure 17:
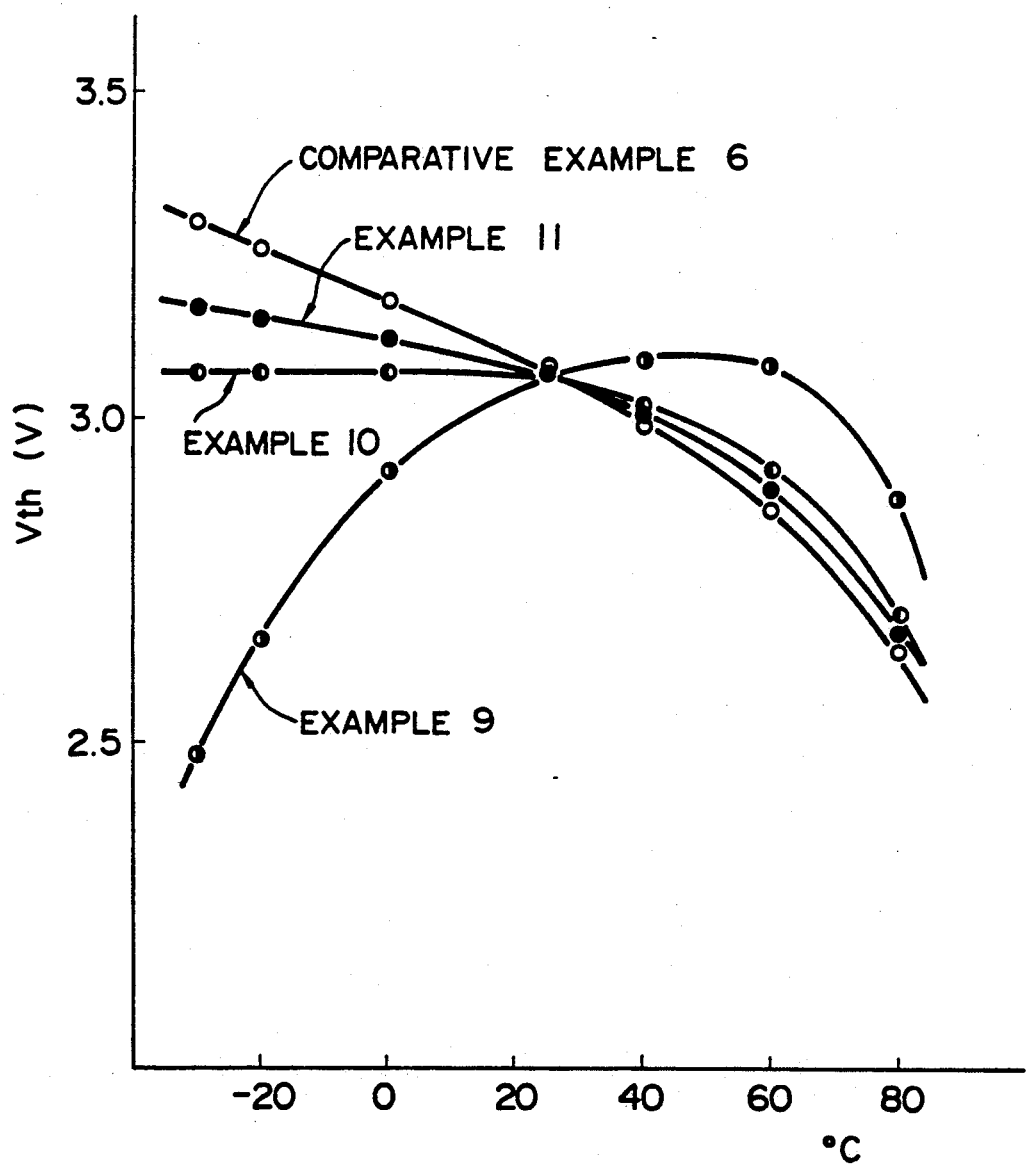

It is seen from FIG. 17 and Table 15 that in the case of Example 9, the temperature dependency of the threshold voltage is contrary to usual one on the lower temperature side, while the absolute value of the $\Delta V_{th}/\Delta t$ is very small on the higher temperature side. In the cases of Examples 10 and 11, the absolute values of the $\Delta V_{th}/\Delta t$ are far smaller than that in the case of Comparative example 6 on the lower temperature side although there are no large difference therebetween on the higher temperature side. Particularly in the case of Example 10, they are constant irrespective of temperature on the lower temperature side.

As described above, by combining an optically active substance of the formula (Ia) with an optically active substance of the formula (II) both having the same twist sense, it is possible to control the temperature dependency of the twistability and also to reduce the temperature dependency of the threshold voltage.

EXAMPLE 12

The above optically active substance B-12 belonging to the group of compounds of the formula (III) and disclosed in the Japanese patent application laid-open No. Sho 61-43, which substance is obtained using S(+)-2-pentanol as a starting raw material and has a left twist sense, and the optically active substance C-9 having the same twist sense as that of the former substance were added in varied mixing proportions but so as to give a total quantity of 1% by weight to the nematic liquid crystal composition (A), to measure the temperature dependency of the twistability $P^{-1}$.

The change of $\Delta P^{-1}{}_{20-70}$ in varied mixing proportions of B-12 and C-9 is shown in FIG. 18. When the quantity of B-12 added is 0.57% by weight, $\Delta P^{-1}=0$, and the range of the quantities thereof added in which $\Delta P^{-1} \approx 0$ ($-0.1 \leq \Delta P^{-1} \leq 0.1$) is as very broad as 0.14~0.74% by weight.

In comparison of Example 12 with Comparative examples 4 and 5, the range of the mixing proportions in which $\Delta P^{-1} \approx 0$ is also very broad in Example 12. According to the prior art, optically active substances having the twist senses which are opposite to one another are mixed together so that the range in which $\Delta P^{-1} \approx 0$ is in the vicinity where $\Delta P^{-1}$ is divergent, whereby the range of the mixing proportion in which $\Delta P^{-1} \approx 0$ is necessarily very narrow, and in order to make the intrinsic pitch constant irrespective of temperature, the very delicate mixing proportion should be exactly determined. According to the present invention, however, by mixing and adding optically active substances both having the same twist sense, it is possible to prepare a nematic liquid crystal composition of $\Delta P^{-1} \approx 0$; hence it has become very easy to control the temperature dependency of the intrinsic pitch.

Further, in comparison of the value of the twistability at 20° C. in the case of $\Delta P^{-1} \approx 0$ in Example 12 with that in Comparative example 4, the results shown in Table 16 are obtained.

TABLE 16

|  | Example 12 | Comparative example 4 |
|---|---|---|
| $\Delta P^{-1}$ 20-70 | 0.01 | 0.14 |
| $P^{-1}$ (20) | 0.040 | 0.021 |

The value of $P^{-1}{}_{(20)}$ in the case of Comparative example 4 is about a half of that in the case of Example 12. In short, in the case of Example 12, a smaller quantity of optically active substances may be sufficient as compared with that in the case of Comparative example 4.

EXAMPLE 13

The above optically active substance B-15 belonging to the group of the compounds of the formula (IV) and disclosed in Japanese patent application No. Sho 60-51512/1985 filed by Chisso Corporation, which substance is obtained using S(+)-2-octanol as a starting raw material and has a left twist sense, and the above optically active substance C-9 having the same twist sense as that of the former substance, were added in varied mixing proportions but so as to give a total quantity of 1% by weight, to the above nematic liquid crystal composition (A) to measure the temperature dependency of the twistability $P^{-1}$ of the resulting liquid crystal composition. The change of $\Delta P^{-1}{}_{20-70}$ in varied mixing proportions of the compounds B-15 and C-9 is shown in FIG. 19. When the quantity of B-15 added is 0.63% by weight. $\Delta P^{-1}=0$, and the range of the quantities thereof added in which $\Delta P^{-1} \approx 0$ (i.e. $-0.1 \leq \Delta P^{-1} \leq 0.1$) is as very broad as 0.1~0.88% by weight.

In the case of Example 13, the range of the mixing proportions in which $\Delta P^{-1} \approx 0$ is much broader than those in the cases of Comparative examples 4 and 5; hence it is very easy to control the temperature dependency of the intrinsic pitch.

Further, the value of the twistability $P^{-1}$ at 20° C. in the mixing proportion in which $\Delta P^{-1} \approx 0$ was compared with that in Comparative example 4. The results are shown in Table 17.

TABLE 17

|  | Example 13 | Comparative example 4 |
|---|---|---|
| $\Delta P^{-1}$ 20-70 | 0.01 | 0.14 |
| $P^{-1}$ (20) | 0.046 | 0.021 |

The value of $P^{-1}{}_{(20)}$ in Example 13 is twice or more the value in Comparative example 4. In short, in the case of Example 13, a smaller quantity of the optically active substance may be sufficient as compared with that in Comparative example 4.

EXAMPLE 14

Figure 20:
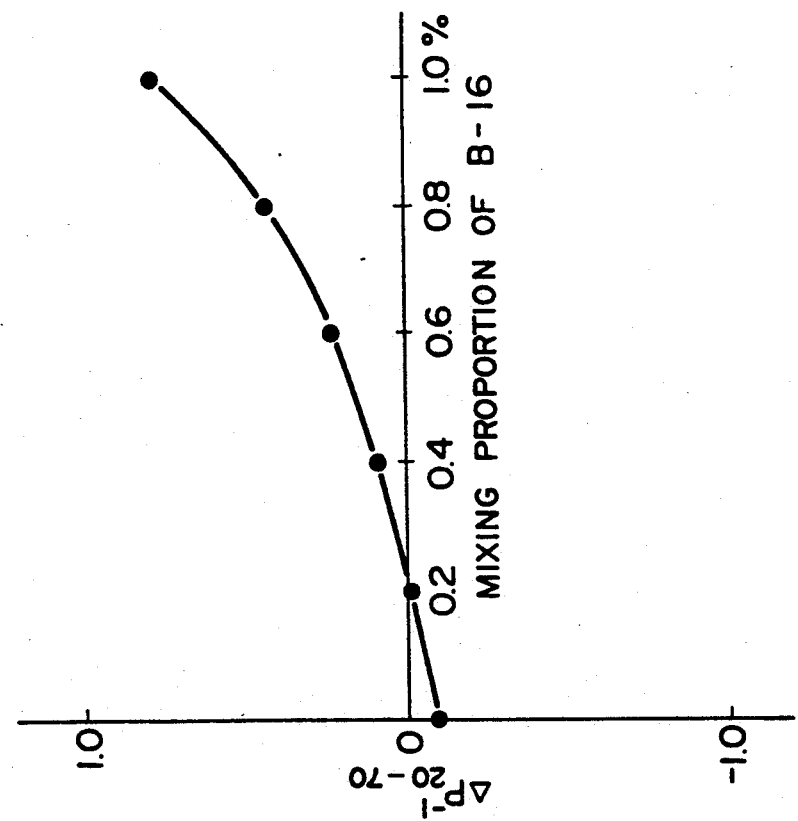

The above optically active substance B-16 belonging to the formula (V), obtained using R(−)-2-octanol as a starting raw material and having a right twist sense, and an optically active substance C-12 having the same formula as that of the former substance C-9 but having a right twist substance, were added in varied mixing proportions but so as to give a total quantity of 1% by weight to the above nematic liquid crystal composition (A), to measure the temperature dependency of the twistability $P^{-1}$ of the resulting liquid crystal composition. The values of $\Delta P^{-1}{}_{20-70}$ in varied mixing proportions are shown in FIG. 20. When the quantity of B-16 added is 0.22% by weight, $\Delta P^{-1}=0$, and the range of the quantities thereof added in which $\Delta P^{-1} \approx 0$ ($-0.1 \leq \Delta P^{-1} \leq 0.1$) is as broad as 0.0~0.41% by weight.

In this Example, the range of the mixing proportions in which $P^{-1} \approx 0$ is much broader than that in Comparative examples 4 and 5; hence it is very easy to control the temperature dependency of the intrinsic pitch. Further the value of $P^{-1}$ at 20° C. in the case of $\Delta P^{-1}=0$ was roughly estimated employing the above equation (3). The results are shown in Table 18.

TABLE 18

|  | Example 14 | Comparative example 4 |
|---|---|---|
| $P^{-1}$ (20) | 0.048 | 0.028 |

The value of $P^{-1}{}_{(20)}$ in Example 14 is about twice the value in Comparative example 4. This indicates that as apparent from the equation (1), in order to obtain a definite intrinsic pitch, the quantity of optically active substances added in Example 14 may be sufficient to be about a half of that in Comparative example 4. The fact that a small quantity of optically active substances added may be sufficient affords two advantages that the resulting composition is cheap as much and there is no influence upon the characteristics of the original liquid crystal composition.

EXAMPLE 15

Figure 21:
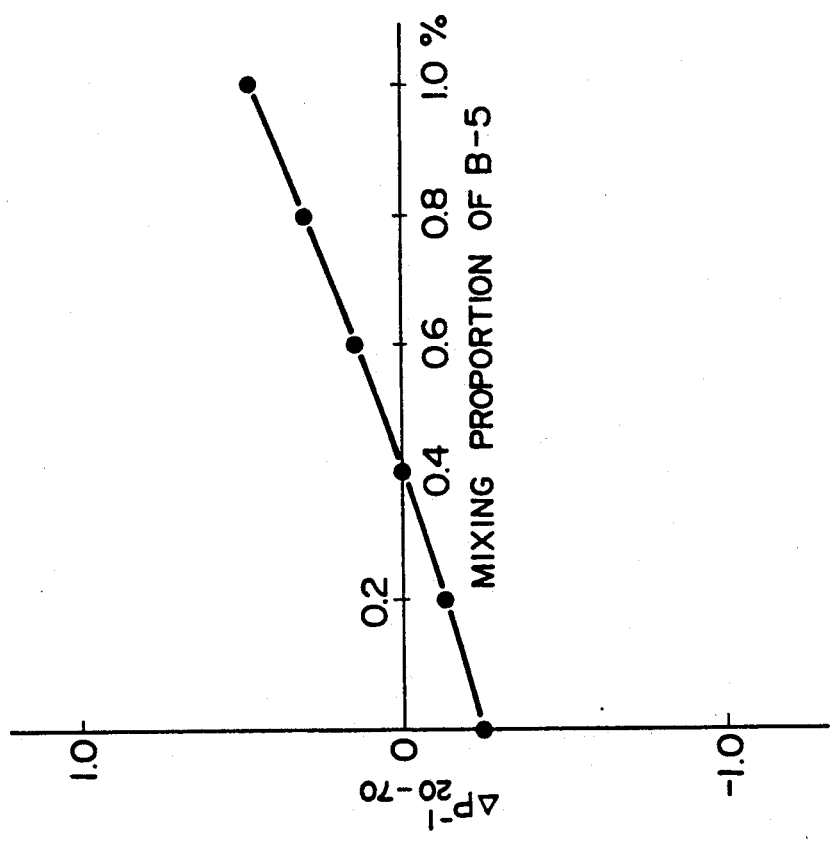

The above optically active substances B-5 and C-3 were added in varied mixing proportions but so as to give a total quantity of 1% by weight to the above nematic liquid crystal composition (A) to measure the temperature dependency of the twistability $P^{-1}$ of the resulting liquid crystal composition. The values of $\Delta P^{-1}{}_{20\text{-}70}$ in varied mixing proportions are shown in FIG. 21. When the quantity of B-5 added is 0.40% by weight, $\Delta P^{-1}=0$, and the range of the mixing proportions in which $\Delta P^{-1}\approx 0$ ($-0.1 \leq \Delta P^{-1} \leq 0.1$) is as broad as 0.30~0.55% by weight. Further, the range of the mixing proportions in which $\Delta P^{-1} \geq 0.1$ is as very broad as 0.55-1.0% by weight.

In comparison of Example 15 with Comparative example 5, the range of the mixing proportion in which $\Delta P^{-1} \approx 0$ in the case of Example 15 is broader than that in the case of Comparative example 5; hence it is easy to make the intrinsic pitch P constant irrespective of temperature. Further, since the range of the mixing proportions in which $\Delta P^{-1} \geq 0.1$ in the case of Example 15 is broader than that in the case of Comparative example 5, it is easy to control the temperature dependency of the intrinsic pitch P to thereby reduce the temperature dependency of the threshold voltage $V_{th}$. Further, the values of $P^{-1}$ at 20° C. in the case of $P^{-1}=0$ were roughly estimated. The results are shown in Table 19.

TABLE 19

|  | Example 15 | Comparative example 5 |
|---|---|---|
| $P^{-1}$ (20) | 0.048 | 0.032 |

The value of $P^{-1}{}_{(20)}$ in Comparative example 5 is considerably smaller than that in Example 15. In short, since the quantity of optically active substance added in Example 15 may be sufficient to be smaller than that in Comparative example 5, Example 15 is superior in that the resulting composition is cheap and the influence upon the characteristics of the original nematic liquid crystal composition is small.

When the composition is applied to SBE mode, it is necessary to make the value of the intrinsic pitch P about 10 μm, taking a usual cell thickness of about 7 μm into account. In order to make the P value 10 μm, the total addition quantity is 2.5% by weight in the case of Example 12; 2.2% by weight in the case of Example 13; 2.1% by weight in the case of Example 14; and 2.1% by weight in the case of Example 15. On the other hand, in order to make the P value 10 μm, the total addition quantity is 4.8% by weight in the case of Comparative example 4.

Since the optically active substance C-1 of Comparative example 4 is in the form of a transparent liquid at room temperature, the NI point of the resulting liquid crystal composition considerably lowers due to considerable increase in the quantity thereof added. In order to prevent the composition from lowering the upper limit temperature of the nematic range, it is necessary to add another liquid crystal compound having a high clearing point (a high temperature liquid crystal compound).

Since high temperature liquid crystal compounds generally have a high visocisity, the viscosity of the resulting liquid crystal composition rises, and further since the optically active substances themselves have a high viscosity, the viscosity of the liquid crystal composition rises considerably so that such a viscosity rise brings about a drawback of reducing the response speed.

In the case of the above TN mode, an intrinsic pitch of about 100-200 μm is generally used, and so a small addition quantity may be sufficient; hence the effect upon the N-I point or the viscosity is small. Whereas, in the case of SBE mode or the like wherein a shorter pitch is required, the addition quantity increases to a large extent. Nevertheless, it is desired to inhibit bad influence due to addition of optically active substances to the utmost.

Examples 12-15 are directed to the case where an optically active compound as expressed by the formula (III) or (V), and having a $\Delta P^{-1}{}_{20\text{-}70}$ value which is positive but not so large, is combined with an optically active substance having the same twist sense as that of the former substance, and also having a $\Delta P^{-1}{}_{20\text{-}70}$ value which is negative value and relatively small.

From the results of these Examples it is seen that for the purpose of being free from the temperature dependency of the intrinsic pitch P in order to use the compositions for SBE mode, DGH mode or PC mode, addition of an optically active substance having a positive and small $\Delta P^{-1}$ value and an optically active substance having the same twist sense as that of the former substance and also having a negative and small $\Delta P^{-1}$ value, broadens the range of the mixing proportion in which $\Delta P^{-1} \approx 0$; hence the object is very easily attained. Further, the optically active components both are preferred to have a shorter pitch at room temperature, because a smaller addition quantity is required.

As described above, it is commercially very important that addition of only a small quantity of optically active substances makes it possible to very easily control the intrinsic pitch of nematic liquid crystal compositions.

What we claim is:

1. A nematic liquid crystal composition comprising: (i) an optically active component which makes positive the temperature dependency of the twistability in terms of the reciprocal of the intrinsic helical pitch thereof, of the cholesteric phase induced when singly added to a nematic liquid crystal and which consists of one optically active substance or at least two optically active substances having the same helical twist sense to one another, said optically active substances being selected from the group consisting of compounds expressed by the formula (III), compounds expressed by the formula (IV), compounds expressed by the formula (V), a compound expressed by the formula (B-7) and a compound expressed by the formula (B-11),

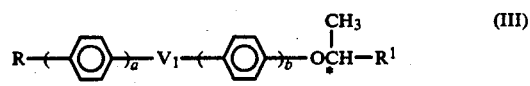

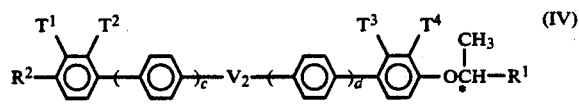

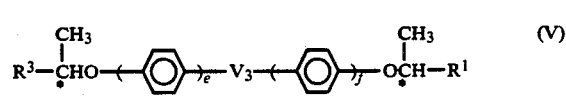

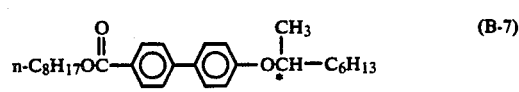

-continued

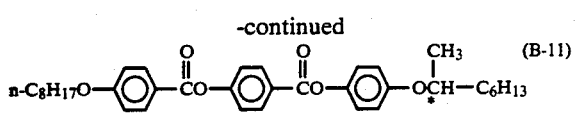

wherein, in the formula (III),
R represents an alkyl group or an alkoxy group each of 1 to 15 carbon atoms or a cyano group;
$R^1$ represents a linear chain alkyl group of 2 to 10 carbon atoms;
a represents an integer of 0, 1 or 2;
b represents an integer of 1 or 2;
the value of (a+b) is 2 or 3;
$V_1$ represents a single bond when a=0, and when a is 1 or 2, $V_1$ represents —COO—, —OCO—, —CH$_2$O—, —OCH$_2$— or —CH$_2$CH$_2$—;
in the formula (IV),
$R^1$ represents a linear chain alkyl group of 2 to 10 carbon atoms;
$R^2$ represents an alkyl group or an alkoxy group each of 1 to 15 carbon atoms, a cyano group or a halogen atom;
$T^1$, $T^2$, $T^3$ and $T^4$ each independently represents a hydrogen atom, a halogen atom or a cyano group;
c and d each represent an integer of 0 or 1; and
$V_2$ represents a single bond, —COO—, or —OCO—;
and in the formula (V),
$R^1$ and $R^3$ each independently represent a linear chain alkyl group of 2 to 10 carbon atoms;
e represents an integer of 0, 1 or 2;
f represents an integer of 1 or 2;
the value of (e+f) is 1 to 3;
$V_3$ represents a single bond when e=0, and when e is 1 or 2, $V_3$ represents —COO— or —CH$_2$O—, and (ii) at least one nematic liquid crystal compound, said optically active component being contained in a quantity in the range of 0.05 to 10% by weight in said composition.

2. A nematic liquid crystal composition according to claim 1 wherein said optically active substances are expressed by the formula (III) in claim 1.

3. A nematic liquid crystal composition according to claim 1 wherein said optically active substances are expressed by the formula (IV) in claim 1.

4. A nematic liquid crystal composition according to claim 1 wherein said optically active substances are expressed by the formula (V) in claim 1.

5. A liquid crystal display element comprising a liquid crystal composition as set forth in claim 1.

6. A liquid crystal display element comprising a liquid crystal composition as set forth in claim 2.

7. A liquid crystal display element comprising a liquid crystal composition as set forth in claim 3.

8. A liquid crystal display element comprising a liquid crystal composition as set forth in claim 4.

* * * * *